(12) United States Patent
Chen et al.

(10) Patent No.: US 8,765,947 B2
(45) Date of Patent: *Jul. 1, 2014

(54) PREPARATION METHOD OF ROSUVASTATIN CALCIUM AND ITS INTERMEDIATES

(71) Applicant: Changzhou Pharmaceutical Factory, Jiangsu (CN)

(72) Inventors: Benshun Chen, Jiangsu (CN); Bing Wang, Jiangsu (CN); Xiaofeng Jin, Jiangsu (CN); Lin Zou, Jiangsu (CN)

(73) Assignee: Changzhou Pharmaceutical Factory, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/785,960

(22) Filed: Mar. 5, 2013

(65) Prior Publication Data

US 2013/0197224 A1    Aug. 1, 2013

Related U.S. Application Data

(62) Division of application No. 12/994,520, filed on Feb. 10, 2011.

(30) Foreign Application Priority Data

May 27, 2008 (CN) .......................... 2008 1 0110709
May 27, 2008 (CN) .......................... 2008 1 0110711

(51) Int. Cl.
   *C07D 239/02* (2006.01)

(52) U.S. Cl.
   USPC ........................................................ 544/297

(58) Field of Classification Search
   USPC ........................................................ 544/297
   See application file for complete search history.

(56) References Cited

U.S. PATENT DOCUMENTS

| 7,612,203 | B2 | 11/2009 | Niddam-Hildesheim et al. |
| 2007/0255060 | A1 | 11/2007 | Okada et al. |
| 2008/0188504 | A1 | 8/2008 | Casar et al. |
| 2011/0124864 | A1 | 5/2011 | Chen |

FOREIGN PATENT DOCUMENTS

| CN | 1763015 A | 4/2006 |
| CN | 1872841 A | 12/2006 |
| CN | 1898233 A | 1/2007 |
| CN | 101376647 A | 3/2009 |
| EP | 0 521 471 A1 | 1/1993 |
| EP | 1 035 127 A1 | 9/2000 |
| WO | WO 00/42024 | 7/2000 |
| WO | WO 00/49014 | 8/2000 |
| WO | WO 01/54668 A1 | 8/2001 |
| WO | WO 01/54669 A1 | 8/2001 |
| WO | WO 01/60804 A1 | 8/2001 |
| WO | WO 02/41895 A1 | 5/2002 |
| WO | WO 03/087112 A1 | 10/2003 |
| WO | WO 03/097614 A2 | 11/2003 |
| WO | WO 2004/014872 A1 | 2/2004 |
| WO | WO 2004/103977 A2 | 12/2004 |
| WO | WO 2004/108691 A1 | 12/2004 |
| WO | WO 2005/023778 A2 | 3/2005 |
| WO | WO 2005/042522 A1 | 5/2005 |
| WO | WO 2006/079611 A1 | 8/2006 |
| WO | WO 2006/091771 A2 | 8/2006 |
| WO | WO 2006/136408 A2 | 12/2006 |
| WO | WO 2007/000121 A1 | 1/2007 |
| WO | WO 2007/022488 A2 | 2/2007 |
| WO | WO 2007/099561 A1 | 9/2007 |

OTHER PUBLICATIONS

Goodman and Gilman, the Pharmacological Basis of Therapeutics, 9th Edition, 1996, pp. 879-881.

Watanabe et al., "Synthesis and Biological Activity of Methanesulfonamide Pyridmidine- and N-Methanesulfonyl Pyrrole-Substituted 3,5-Diydroxy-6-heptenoates, a Novel Series of HMG-CoA Reductase Inhibitors", Biorganic & Medicinal Chemistry, vol. 5, No. 2, 1997, pp. 437-444.

"The Lipid Research Clinics Coronary Primary Prevention Trial Results", Lipid Research Clinics Program, JAMA, Jan. 20, 2004, vol. 251, No. 3, pp. 351-364.

Application and File history for U.S. Appl. No. 12/994,520, filed Feb. 10, 2011. Inventors: Benshun Chen et al.

Primary Examiner — Kamal Saeed
Assistant Examiner — Ebenezer O Sackey
(74) Attorney, Agent, or Firm — Patterson Thuente Pedersen, P.A.

(57) ABSTRACT

A preparation method of rosuvastatin calcium (Formula 1), which can be used for the production of medicament lowering the levels of LDL-cholesterol and triglycerides in vivo, is provided. Such preparation method is suitable for industrial production. Furthermore, the intermediate crystallines used in the preparation method are provided.

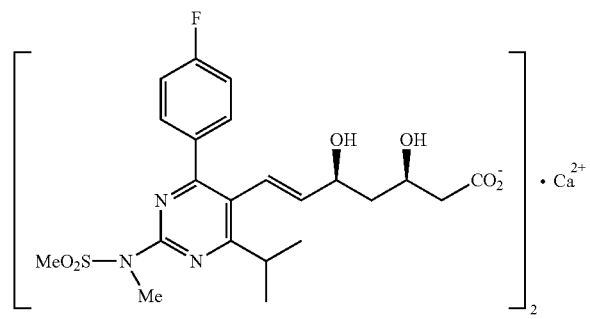

18 Claims, 3 Drawing Sheets

PREPARATION METHOD OF ROSUVASTATIN CALCIUM AND ITS INTERMEDIATES

RELATED APPLICATION

This application is a division of application Ser. No. 12/994,520 filed Feb. 10, 2011, which in turn is a National Phase entry of PCT Application No. PCT/CN2009/072018, filed May 27, 2009, which claims priority from Chinese Application Number 200810110711.9, filed May 27, 2008, and Chinese Application Number 200810110709.1, filed May 27, 2008, the disclosures of which are hereby incorporated by reference herein in their entirety.

FIELD OF THE INVENTION

The present invention belongs to the field of pharmaceutical chemistry, in particular, it relates to a preparation method of industrialized Rosuvastatin calcium (Formula 1), wherein this calcium salt is used for the production of medicines that lowering LDL-cholesterol and triglyceride in vivo. Furthermore, the present invention relates to the intermediate crystal of this preparation method.

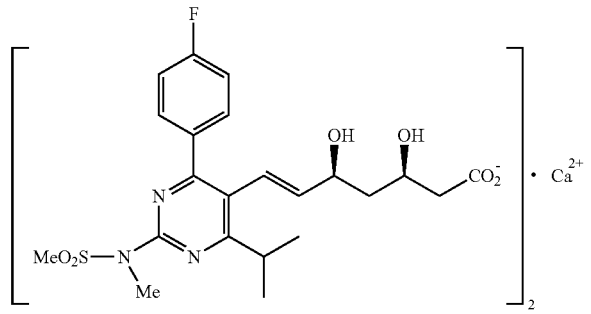

(Formula 1)

TECHNICAL BACKGROUND OF THE INVENTION

The formation of coronary artery disease that blocks blood circulation is closely related to the high levels of low density lipoprotein (LDL) in the blood (Goodman and Gilman, the Pharmacological Basis of Therapeutics, Page 879 (9$^{th}$ Edition, 1996)). At present, statins are the most effective drugs to reduce the concentration of LDL particles in the blood for patients having the risk for cardiovascular disease, and therefore they are used for the treatment of hypercholesterolemia, hyperlipoproteinemia and atherosclerosis, etc. Statins inhibit the biosynthesis of cholesterol by their competitive inhibition to 3-hydroxy-3-methyl-glutaryl coenzyme A ("HMG-CoA") reductase, which results in reduction in the concentration of LDL particles in the blood, and therefore reduces the possibility of suffering from coronary artery disease (J. A. M. A. 1984, 251, 351-74).

At present, there is a number of statins with different structures available in the market, including Lovastatin, Simvastatin, Pravastatin, Fluvastatin, Cerivastatin, Atorvastatin, Rosuvastatin and Pitavastatin, etc. As a HMG-CoA reductase inhibitor, Rosuvastatin calcium (that is, (E)-7-[4-(4-fluorophenyl)-6-isopropyl]-2-[methyl(methyl sulfonyl)amino]pyrimidyl-5-(3R,5S)-3,5-dihydroxy-6-heptenoic calcium) is a so-called super statin, and compared with the first generation statins, Rosuvastatin calcium is more effective in reducing the concentration of LDL-cholesterol and triglyceride in vivo.

The commercial name of Rosuvastatin is CRESTOR, and it should be taken orally once per day for the treatment of hyperlipoidemia (Ann Rep, Shionogi, 1996; Direct communications, Shionogi, Feb. 8, 1999 and Feb. 25, 2000). The daily dosage can be about 5 mg to about 40 mg. As for patients who do not require a considerable reduction of LDL-C or patients who have predisposing factors of myonosus, the recommended dosage is 5 mg, as for common patients, the recommended dosage is 10 mg, as for patients who have hyper cholesterolemia and require a relatively high lipid target (>190 mg/dL), the recommended dosage is 20 mg, while for patients who do not show response at low dosage, the recommended dosage is 40 mg. Rosuvastatin Calcium could also be used for the treatment of hypercholesterolemia, hyperproteinemia and atherosclerosis.

Synthesis and preparation of Rosuvastatin calcium was first disclosed in EP 0521471, wherein 4-(4-fluorophenyl)-6-isopropyl-2-(N-methyl-N-methyl sulfonyl amino)-5-pyrimidinecarbaldehyde and Methyl (3R)-3-(tert-butyldimethylsilyloxy)-5-oxo-6-triphenylphosphoranylidene hexanate reacted and refluxed in the presence of acetonitrile, subsequently, silyl group underwent pyrolysis under the action of HF, the obtained compound was reduced by NaBH$_4$, as a result, Rosuvastatin methyl ester was formed. Said ester was hydrolyzed by NaOH at room temperature in the presence of ethanol, at the end of the reaction, ethanol was removed, ether was added and Rosuvastatin sodium was obtained. The obtained Rosuvastatin sodium was dissolved in water under a nitrogen atmosphere. CaCl$_2$ was added to said water solution, and precipitate of Rosuvastatin calcium was obtained. Wherein, the method disclosed by said patent required column chromatography to be carried out, which leads to increase in the complexity of process and production cost, and therefore it is not conducive to the goal that reducing the medical cost to benefit more patients. Bioorganic & Medicinal Chemistry, Vol. 5, NO. 2, pp 437-444, 1997 also reported a synthetic method of Rosuvastatin calcium, and said method was similar to that disclosed in EP0521471.

In EP0521471, even after column chromatography, the obtained Rosuvastatin methyl ester was still syrupy, this syrupy Rosuvastatin methyl ester was difficult to be purified by recrystallization, its purity was lower than 97% and the content of diastereomer was above 5%. EP0521471 described the formation of Rosuvastatin sodium via hydrolysis in ethanol, the obtained was beat with ethyl ether and crystallized Rosuvastatin sodium crystal powder was obtained, however, the formation of crystallized solid powder could only be realized in the laboratory by beating with ethyl, and it was very difficult to scale up and be applied to large-scale industrialized production, furthermore, the purification effect is not satisfactory due to the fact that diastereomer could not be separated by this process. EP0521471 disclosed the direct synthesis of Rosuvastatin calcium from Rosuvastatin sodium, however, these steps make the calcium salt difficult to be purified by recrystallization of Therefore, the content of diastereomer in Rosuvastatin calcium obtained from Rosuvastatin methyl ester was around 0.8%, several unknown impurities with concentration of above 0.1% were observed, leading to difficulty in obtaining highly purified Rosuvastatin calcium and industrialization of Rosuvastatin calcium. Furthermore, since the compound of Formula 3 presented in said EP0521471 and its improved method is taken in excess, the utilization rate of high cost compound as shown in Formula 3 was lower than 50% and the production cost was strongly affected. Accordingly, it is required to purify the compound as shown in Formula 4 or compound as shown in Formula 5 by column chromatography in current technique, otherwise purification is very difficult to be realized via direct recrystallization. However, the production cost of column chromatography is high and it is difficult to be applied in industrialization.

Improvements of synthetic process of EP0521471 have been reported. For instance, international application WO03087112 improved phosphorus ylide reagent based on EP0521471, wherein diester glutarate was converted to monoester glutarate via biological enzyme method, subsequently, the resultant was converted into tert-butyl ester containing silane blocking group, as a result, phosphorus ylide reagent different from that of EP0521471 in term of ester group was obtained; WO03097614 disclosed improvement of synthetic process of main-chain aldehyde N-[4-(4-fluorophenyl)-5-formyl-6-(1-methylethyl)-2-pyrimidyl]-N-methyl-methansulfnamide, however, preparation method of final product was similar to EP0521471; international application WO2005023778 reported industrial preparation method of Rosuvastatin calcium in substance free of impurities, however, the synthesis method of Rosuvastatin ester was still similar to that disclosed in EP0521471, furthermore, no detailed information was available on how to prepare highly purified Rosuvastatin ester; international application WO2006091771 described improvement of synthesis of Rosuvastatin calcium, wherein the major difference between WO2006091771 and EP0521471 was that ester group of side chain was replaced by ter-butyl ester group, but it was still very difficult to prepare highly purified Rosuvastatin according to the method of said application.

Besides preparation methods based on EP0521471, other synthetic methods which are different from the synthetic route of EP0521471 have been reported as well. For instance, international application WO0049014 (priority date: Feb. 17, 1999) reported a preparation method of Rosuvastatin calcium. Wherein, tert-butyl 2-[(4R,6S)-6-formyl-2,2-dimethyl-1,3-dioxan-4-yl]acetate with two chiral centers was acted as side chain, said chain reacted with phosphorus ylide reagent diphenyl[4-(4-fluorophenyl)-6-isopropyl-2-[methyl (methylsulfonyl) amino]pyrimidin-5-ylmethyl]phosphine oxide and took place Wittig condensation, subsequently, acetonylidene blocking group was removed via acidic hydrolysis, the obtained was saponified in the presence of alkali, in this way, sodium salt was converted to calcium salt.

EP1035127 disclosed a preparation method of intermediate of Rosuvastatin calcium, wherein said intermediate can be used in the synthetic route of WO0049014; WO2004108691 described improvement of the formation of Rosuvastatin salt from Rosuvastatin calcium, however, said improvement was based on the preparation method of Rosuvastatin calcium reported in WO0049014; international application WO2005042522 reported a preparation method based on WO0049014, wherein the crystallized intermediate was separated and used for the synthesis of Rosuvastatin.

Furthermore, improvements of the synthesis of Rosuvastatin calcium and its intermediate have been reported. For instance, international application WO0042024 focused on some specific crystal forms of Rosuvastatin calcium; international applications WO0154668 and WO0154669 disclosed a composition of Rosuvastatin calcium; international application WO0160804 described crystalline salt of Rosuvastatin, wherein said crystalline salt could be used for the purification of Rosuvastatin calcium; international application WO0241895 disclosed the use of Rosuvastatin in the treatment of an indication, that is heterozygous familial hyperlipidemia; international application WO2004014872 described improvements of the salt formation of Rosuvastatin calcium, wherein the improved processing conditions were used for preparation of highly filtrated solid; international application WO2004103977 disclosed improvement of synthesis of pyrimidyl heterocycle intermediate of Rosuvastatin calcium; international application WO2007000121 reported improvement on the preparation of Rosuvastatin calcium from Rosuvastatin lactone intermediate; international application WO2006079611 described other crystal forms of Rosuvastatin calcium (crystal form B and C); Chinese patent application CN1872841 disclosed recrystallization method of compound as shown in Formula 5, wherein said compound was recrystallized under the action of mixed solvent containing methylbenzene and ethyl ether, as a result, intermediate with purity of higher than 98% was obtained, however, Rosuvastatin methyl ester still required to be purified by column chromatography, the purity of said Rosuvastatin methyl ether was very low, the content of diastereomer was 0.5% and the total content of other impurities was 1%; international application WO2006136408 reported a preparation method of Rosuvastatin calcium and other Rosuvastatin salt from Rosuvastatin ester; international application international application WO2007022488 reported crystalline intermediate of Rosuvastatin and a process for the preparation thereof.

SUMMARY OF THE INVENTION

Based on the process route and its related patent applications, the present invention provides an improved preparation method of Rosuvastatin calcium after intensive study, wherein asymmetric reduction of borane is optimized, and crude Rosuvastatin ester with relatively low content of diastereomer is obtained. After said crude Rosuvastatin ester forms water soluble sodium salt via hydrolysis, the water insoluble impurities are removed via extraction thus said crude Rosuvastatin ester is converted to relatively purified ester with high yield, subsequently, highly purified Rosuvastatin ester is formed via crystallization, the obtained is then converted to Rosuvastatin calcium with high yield. In this way, the content of the impurities is effectively controlled, problems involved in the preparation of highly purified Rosuvastatin calcium, especially Rosuvastatin calcium with low content of diastereomer is successfully solved. Furthermore, the present invention is suitable for large scale production, problem involved in the preparation of ICH qualified raw materials is solved. Moreover, the present invention also provides an intermediate used in the improved preparation method.

The present invention aims at providing a synthetic method of Rosuvastatin calcium with optimization of synthesis conditions, which is based on the improvement of the synthetic route disclosed in EP0521471, wherein, the type of reagent, the ratio between reagents and the reaction conditions are optimized in present invention. In the large-scale industrial production, both the yield and quality (purity) of Rosuvastatin calcium provided in the present invention are higher than those of EP0521471. It is particularly surprising that preparation method of Rosuvastatin calcium provided in the present invention does not require operations (such as column chromatography) that are difficult for industrialization, which leads to a lowering in production cost in comparison with the synthetic route disclosed in EP0521471, thus the present invention is more suitable for industrialization. Moreover, due to the fact that the yield of esterification of Rosuvastatin acid is relatively high and the conversion rate is as high as 99.0% under optimized conditions, although more steps are involved in the present invention, the yield is still relatively high, ester that is difficult to crystallize is converted to ester that is easy to crystallize, at the same time diastereomer and other impurities are removed during said step by recrystallization and other simple steps.

In summary, the scope of the present invention comprising the following aspects:

In the first aspect, the present invention provides a preparation method of compound shown as Formula 1, wherein it comprises:

1) Compound shown as Formula 2 reacts with compound shown as Formula 3 take place Wittig condensation, as a result, compound shown as Formula 4 is obtained:

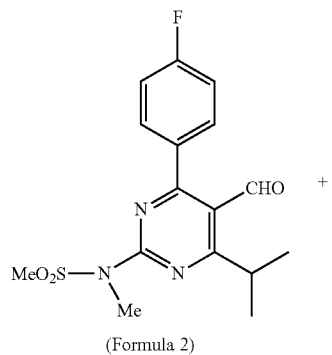

(Formula 2)

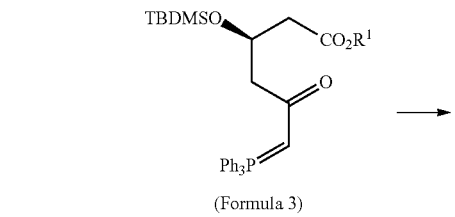

(Formula 3)

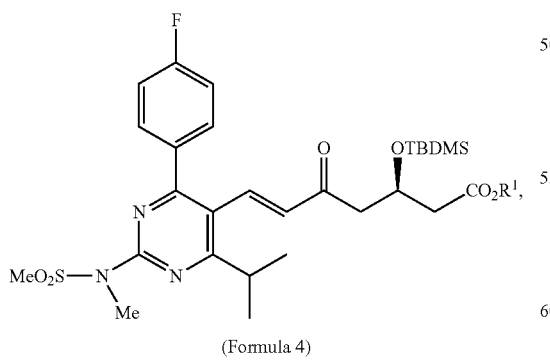

(Formula 4)

Wherein, $R^1$ is low alkyl group;

2) Silane protection group is removed from compound shown as Formula 4 in the presence of HF, as a result, compound shown as Formula 5 is obtained;

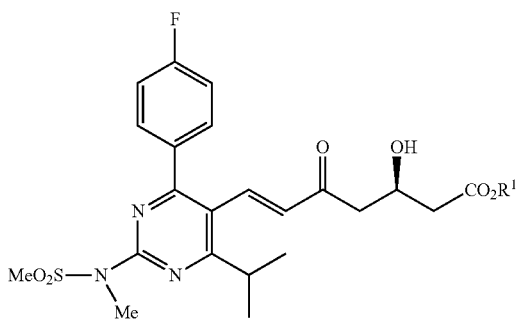

(Formula 5)

3) Compound shown as Formula 5 undergoes asymmetric reduction in the presence of $R^2{}_2BOMe$ and $NaBH_4$, and forms compound shown as Formula 6

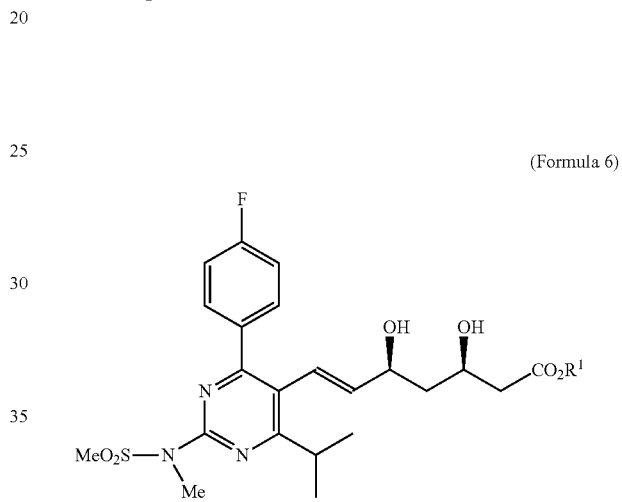

(Formula 6)

Wherein $R^2$ is C2-8 alkyl;

4) Compound shown as Formula 7 is formed via alkaline hydration from compound shown as Formula 6 in the presence of NaOH;

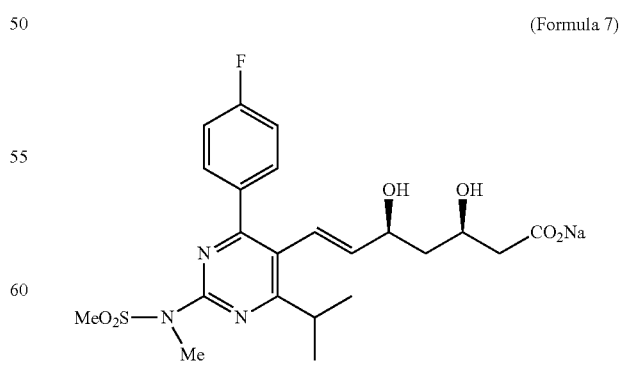

(Formula 7)

5) Compound shown as Formula 8 is formed via acidification from compound shown as Formula 7 in the presence of acid;

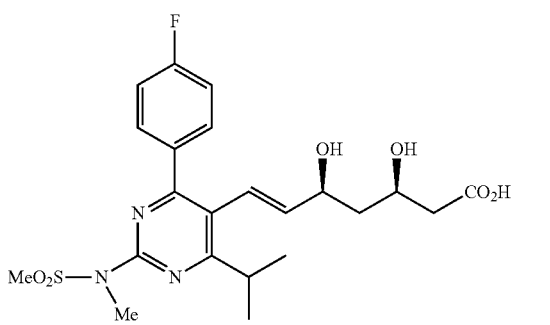

(Formula 8)

6) Esterification is carried out between compound as shown in Formula 8 and halohydrocarbon R³X alkali, as a result, compound as shown in Formula 9 is obtained

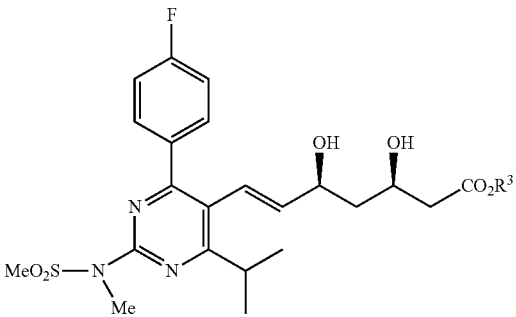

(Formula 9)

Wherein R³ is selected from the group consisting of low alkyl group and benzyl, optionally substituted by hydroxyl group, halogen or benzene, and X is halogen;

7) Compound as shown in Formula 7 is formed via alkaline hydration of compound as shown in Formula 9 in the presence of sodium hydroxide; and 8) Compound as shown in Formula 7 is converted to compound as shown in Formula 1 in the presence of water soluble Calcium salt.

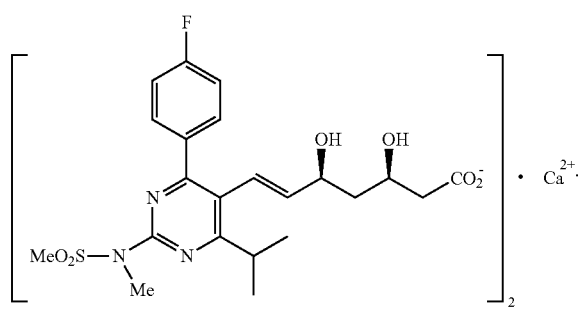

(Formula 1)

In the method of the present invention, wherein the preferred embodiment is in absence of the step of column chromatography. Under the premise that the product quality and the yield are ensured, the present invention is more suitable for industrialization.

In step (1) of present invention, wherein the preferred molar ratio between compound as shown in Formula 3 and compound as shown in Formula 2 is 0.9~1.2:1, and the more preferred molar ratio is 1:1.

Furthermore, in step (1) of the present invention, wherein reaction of said step (1) takes place in the presence of solvent, said solvent is non-ketone organic solvent, and the preferred solvent is selected from the group consisting of acetonitrile, methylbenzene, cyclohexane, n-hexane, n-heptane, HMPA, DMF, DMI, DMSO, chloroform, carbon tetrachloride, carbon dichloride, 1,2-dichloroethane and mixture thereof. The most preferred solvent is acetonitrile. Wherein, the ratio between said solvent and compound as shown in Formula 3 is 0.1~5 (mL/g), the more preferred ratio is 0.3~20 (mL/g) and the most preferred ratio is 0.5 (mL/g).

In step (1) of the present invention, wherein in order to remove byproduct triphenylphosphine oxide, the product obtained from said step (1) is preferably purified by recrystallization, the solvent used in said recrystallization is selected from the group consisting of alkanes, aromatics, halogenated aromatic hydrocarbon or ether, more preferred solvent is selected from the group consisting of cyclohexane, n-hexane, n-heptane, petroleum ether, benzene, methylbenzene, ethyl ether, isopropyl ether, tert-butyl methyl ether, chlorobenzene, o-dichlorobenzene and mixture thereof, and the most preferred solvent is cyclohexane.

In step (2) of the present invention, wherein the product obtained from said step (2) is preferably purified via recrystallization, the solvent used in said recrystallization is selected from the group consisting of alcohol, ether, ester, ketone, aromatic hydrocarbon or alkane and mixture thereof, the more preferred solvent is ethyl ether or a mixture containing acetone and isopropyl ether. Wherein said recrystallization could be multi-step recrystallization, and the solvents used in each recrystallization are different, for example, ethyl ether is used as solvent for the first recrystallization, and a mixture containing acetone and isopropyl ether is used as solvent for the second recrystallization in order to further purify the obtained product.

In step (3) of the present invention, wherein the preferred R² is ethyl group, propyl group, butyl group, isobutyl group, 1,2-dimethyl propyl or cyclohexyl. Furthermore, in order to influence reductant and thus terminate the reaction of said step (3), glacial acetic acid is preferably added to terminate reaction.

In step (4) of the present invention, wherein the reaction of said step (4) proceeds in the presence of solvent, said solvent is selected from the group consisting of THF, alcohol and acetonitrile, and the preferred solvent is acetonitrile; the reaction temperature range of step (4) is between −10 and 80° C., and the preferred reaction temperature range is between 20 and 40° C.; furthermore, the molar ratio between NaOH and compound as shown in Formula 6 is 1.05~2.0:1, and the preferred molar ratio is 1.1:1. Moreover, at the end of step (4), extraction is performed to remove impurities, the product obtained from step (4) is preferably purified via extraction of water-immiscible solvent, and the preferred water-immiscible solvent is ethyl acetate or ethyl ether.

In step (5) of the present invention, wherein the reaction of step (5) proceeds in the presence of solvent, said solvent is selected from the group consisting of ester, ether and halohydrocarbon, and the preferred solvent is ethyl ether.

In step (6) of the present invention, wherein the reaction of step (6) proceeds in the presence of solvent, said solvent is selected from the group consisting of ketone, DMF, DMSO, and HMPA, and the preferred solvent is acetone. Wherein the most preferred halogenated hydrocarbon R³X is 1-bromo-3- methylbutane; the preferred alkali is selected from the group consisting of carbonate, bisulfate, biphosphate, dihydrix phosphate and organic amine, and the most preferred alkali is $K_2CO_3$. The reaction temperature range of said step (6) is between −40 and 80° C., the preferred temperature range is between 0 and 60° C., the more preferred temperature range is between 10 and 50° C., and the most preferred temperature range is between 20 and 40° C.

In step (6) of the present invention, wherein the $R^3$ is preferably low alkyl group; the reaction system preferably contains phase transfer catalyst, the preferred catalyst is quaternary ammonium, crown ether or polyethylene glycol, and the most preferred catalyst is tetrabutyl ammonium bromide.

In step (6) of the present invention, wherein in order to purify the obtained product, the product obtained from step (6) is preferably purified via recrystallization, the solvent of said recrystallization is selected from the group consisting of ether, ester, alcohol and water solution thereof, and the preferred solvent is ethyl ether or isopropyl ether.

In step (7) of the present invention, wherein the reaction of step (7) proceeds in the presence of solvent, said solvent is selected from the group consisting of THF, alcohol and acetonitrile, and the preferred solvent is acetonitrile; the reaction temperature range of step (7) is between −10 and 80° C., and the preferred temperature range is between 20 and 40° C.; furthermore, in the step (7), the molar ratio between NaOH and compound as shown in Formula 6 is 1.05~2.0:1, and the preferred ratio is 1.1:1. Moreover, at the end of step (7), in order to remove the impurities, the product obtained from step (7) is extracted with water-immiscible solvent, and the preferred water-immiscible solvent is ethyl acetate or ethyl ether.

In step (8) of the present invention, wherein the preferred soluble calcium salt is calcium acetate or calcium chloride. The molar ratio between soluble calcium salt and compound as shown in Formula 7 is 1.0~1.2:2, the more preferred ratio is 1.05:2. Wherein, the compound as shown in Formula 7 is more preferably converted to compound calcium acetate as shown in Formula 1 in the presence of calcium acetate.

In step (8) of the present invention, wherein in order to further recover the compound as shown in Formula 1 in the mother liquid, at the end of step (8), compound as shown in Formula 1 is separated, remaining aqueous solution is acidified, subsequently, it is extracted with solvent, alkali is added to dissolve said aqueous solution, and then soluble calcium salt is added, as a result, compound as shown in Formula 1 is obtained, wherein the preferred solvent is ethyl ether, and the preferred soluble calcium salt is calcium acetate.

In the second aspect, the present invention also provides application of said step (6) or step (6) to step (7) in the first aspect of present invention in purification of Rosuvastatin ester, Rosuvastatin lactone or Rosuvastatin salt, wherein Rosuvastatin ester, Rosuvastatin lactone or Rosuvastatin salt is first converted to Rosuvastatin acid, subsequently, step (6) or step (6) to step (7) of said any one of claims of present invention is carried out, the preferred Rosuvastatin salt is Rosuvastatin calcium.

In the third aspect, the present invention provides crystalline intermediate obtained via preparation method in the first aspect of the present invention, wherein:

(3R,5S,6E)-7-[4-(4-fluorophenyl)-6-(1-methyl ethyl)-2-[methyl(methyl sulfonyl)amino]-5-pyrimidyl]-3,5-dihydroxyl-6-methyl heptenoate has spectrum of powder XRD showing peak values at 2θ=8.7, 9.3, 9.6, 17.4, 18.0, 19.5, 21.7, 24.4, 24.7 and 26.3;

(3R,5S,6E)-7-[4-(4-fluorophenyl)-6-(1-methyl ethyl)-2-[methyl(methyl sulfonyl)amino]-5-pyrimidyl]-3,5-dihydroxyl-6-isopentyl heptenoate has spectrum of powder XRD showing peak values at 2θ=9.5, 16.3, 19.3, 20.7 and 20.9; and (3R,5S,6E)-7-[4-(4-fluorophenyl)-6-(1-methyl ethyl)-2-[methyl(methyl sulfonyl)amino]-5-pyrimidyl]-3,5-dihydroxyl-6-isopentyl heptenoate has spectrum of powder XRD showing peak values at 2θ=9.6, 11.9, 16.6, 18.5, 19.2, 19.7 and 20.8.

In the forth aspect, the present invention provides application of said crystalline intermediate in the third aspect of the present invention in the preparation or purification of Rosuvastatin salt, especially in the preparation or purification of Rosuvastatin calcium.

DETAILED DESCRIPTION OF THE DRAWINGS

1. Definition of Terms

Figure 1:
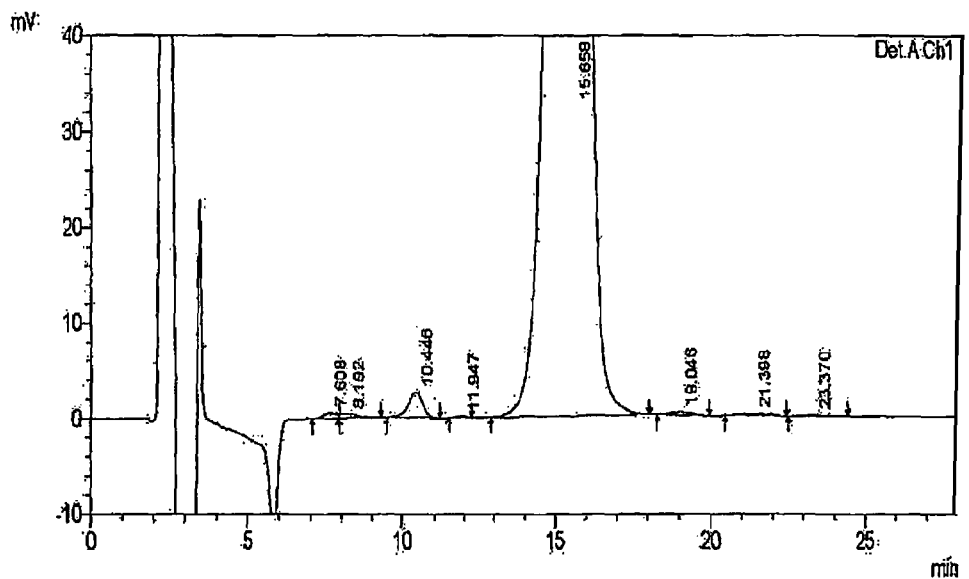
FIG. 1 shows the test results of (3R,6E)-7-[4-(4-fluorophenyl)-6-(1-methyl ethyl)-2-[methyl(methylsulfonyl)amino]-5-pyrimidyl]-3-hydroxyl-5-oxo-6-methyl heptenoate prepared according to an embodiment of the present invention by HPLC.

The terms used in the present invention have common definitions to those skilled in the pharmacochemistry field. Alcohol, ether, crown ether, ester, ketone, aromatic hydrocarbon, alkane and halogen are frequently used chemicals and people skilled in the art should be able to choose said chemicals according to embodiments of the present invention. The preferred alcohol, ether, ester, ketone, aromatic hydrocarbon and alkane should contain less than 10 carbons. Furthermore, the "low alkyl group" of present invention refers to C1-10 alkyl group i.e. the alkyl group containing 1~10 carbons, and the C1-6 alkyl group is preferred.

2. Step (1) of the Present Invention

Large-scale industrial preparation of compound as shown in Formula 2 and compound as shown in Formula 3 could be realized based on EP0521471 and its related improvements, however, large-scale preparation of compound as shown in Formula 4 and compound as shown in Formula 2 is still difficult. Preparation of compound as shown in Formula 4 based on current techniques requires a relatively large amount of expensive compound as shown in Formula 3 (the price of compound as shown in Formula 3 is 5 times higher than that of compound as shown in Formula 2), the molar ratio between compound as shown in Formula 3 and compound as shown in Formula 2 is 1.5:1, the formed compound as shown in Formula 4 has to be purified via column chromatography (or the formed compound as shown in Formula 5 has to be purified via column chromatography, otherwise syrupy material that is difficult to crystallize will be obtained), and therefore the yield is relatively low (taking compound as shown in Formula 2 as an example, the yield of crude product obtained after column chromatography is 71.3%), the utilization rate of compound as shown in Formula 3 is lower than 50%, and the production cost is increased. Wherein, without the application of column chromatography, the byproduct triphenylphosphine oxide is relatively difficult to be removed, and the removal rate is generally lower than 60%.

In order to realize the large-scale industrial production of Rosuvastatin calcium, reaction of step (1) is optimized in the present invention, wherein the ratio of compound as shown in Formula 3 is lowered, as a result, the reaction efficiency is not affected and the utilization rate of compound as shown in Formula 3 is improved. When an excess amount of compound as shown in Formula 3 is present, compound as shown in Formula 2 is difficult to fully convert after the completion of the reaction of step (1). Due to the presence of an excess amount of compound as shown in Formula 3, the introduced impurities strongly influence the crystallization of compound as shown in Formula 2, and therefore purification means that are difficult to be used in industrialization, such as column chromatography have to be applied.

Furthermore, as the melting point of compound as shown in Formula 3 is relatively low, it is difficult to crystallize at lower purity, therefore the removal of triphenylphosphine oxide from compound as shown in Formula 4 via recrystallization is strongly influenced. When the molar ratio between compound as shown in Formula 2 and compound as shown in Formula 3 is 0.9~1.2:1, preferred ratio is 1:1, almost no compound as shown in Formula 3 is left after the completion of the reaction of step (1), in this way, the maximum utilization of compound as shown in Formula 3 is achieved. Even when a small amount of compound as shown in Formula 2 remains, the influence of compound as shown in Formula 2 on the crystallization of compound as shown in Formula 5 is insignificant for its melting point is relatively high and it is easy to crystallize, accordingly compound as shown in Formula 5 could be easily crystallized without the application of column chromatography. Therefore, the impurity removal rate of said step is high, wherein the removal rate of triphenylphosphine oxide is higher than 80%.

The inventors have surprisingly found that the amount of solvent influences the reaction rate and quality of said step (1): when the ratio between said solvent and compound as shown in Formula 3 is 0.1~5 (mL/g), the preferred ratio is 0.3~2.0, and the most preferred ratio is 0.5 (mL/g), the reaction rate is increased, the reaction time is shortened, and the control of impurity is more efficient; when the ratio between said solvent and compound as shown in Formula 3 is 5~20, the reaction rate is lower and the amount of impurity increases.

3. Step (2) of the Present Invention

Compound as shown in Formula 4 and compound as shown in Formula 5 need not to be purified via column chromatography, and compound as shown in Formula 5 could be directly purified via recrystallization with the solvent. Highly purified compound as shown in Formula 5 facilitates the control of follow-up reaction, the quality of Rosuvastatin calcium (impurity control) and the overall yield. Compound as shown in Formula 5 could crystallize in several solvents, and said solvent can be selected from the group consisting of alcohol, ether, ester, ketone, aromatic hydrocarbon, alkane and mixture thereof, the preferred solvent is ethyl ether or a mixture containing acetone and isopropyl ether. Wherein it could be multi-recrystallization, and the solvent used in each recrystallization is different, for instance, ethyl ether is used as solvent for the first recrystallization, and a mixture containing acetone and isopropyl ether is used for the second recrystallization to further refine.

4. Step (3) of the Present Invention

According to EP0521471 and its related improvements, oily Rosuvastatin methyl ester is obtained via reduction of (3R,6E)-7-[4-(4-fluorophenyl)-6-(1-methylethyl)-2-[methyl (methyl sulfonyl)amino]-5-pyrimidyl]-3-hydroxyl-5-oxo-6-methyl heptenoate, and therefore, the obtained is difficult to directly recrystallize. According to said patent, even after the purification of Rosuvastatin methyl ester by column chromatography, the quality of obtained Rosuvastatin calcium is relatively poor, the content of diastereomer is generally greater than 0.5%, and the total content of other impurities is higher than 1.5%. As for asymmetric reduction via sodium borohydride complexing with methoxydiethylborane, although the selectivity is high (generally greater than 98:2), the formation of diastereomer during reduction is still unavoidable, and the content of diastereomer is between 0.5~2.0%, therefore in order to obtain a relatively high diastereomeric excess (de), the obtained has to be purified via recrystallization.

The inventors have found that almost all Rosuvastatin esters can crystallize, however, the properties of these esters, especially their crystallization, are considerably different, wherein Rosuvastatin methyl ester is the most difficult one to crystallize. Generally speaking, when the purity of Rosuvastatin methyl ester is lower than 80%, it is almost impossible to crystallize, when the purity of Rosuvastatin methyl ester is lower than 95%, the crystallization is relatively slow and an inoculating seed has to be added to induce or a relatively long stirring time is necessary, if the purity is high, crystallization in several different solvents is also possible; on the contrary, the crystallization properties of Rosuvastatin ethyl ester, Rosuvastatin propyl ester, Rosuvastatin isopropyl ester, Rosuvastatin n-butyl ester, Rosuvastatin iso-butyl ester and Rosuvastatin tert-butyl ester is relatively good; especially Rosuvastatin isopentyl ester has excellent crystallization, for it is easy to crystallize and precipitate from several solvents even its purity is relatively low. Therefore, recrystallization is not necessary in step (3) of the present invention, and it is performed in later steps on other Rosuvastatin esters which are much easier to crystallize.

THF and methanol could be used as solvent in step (3) of the present invention, wherein dialkyl methoxyborane is added at low temperature (for example −78° C.), subsequently, reductant such as sodium borohydride is added and Rosuvastatin methyl ester is obtained. The selectivity depends on different boron reagent. In general, the larger the alkyl group, the more crowded the space, and as a result, the higher the selectivity, therefore, the dialkyl methoxyborane is preferably selected from the group consisting of diethyl methoxyborane, dipropyl methoxyborane, dibutyl methoxyborane, diisobutyl methoxyborane, di(1,2-dimethyl propyl) methoxyborane or dicyclohexyl methoxyborane. The reaction should proceed at low temperature; and the volume ratio between THF and methanol of mixed solvent is 2:1~5:1, and the preferred ratio is 3:1~4:1; the preferred ratio between volume of the solvent and mass of the compound as shown in Formula 5 is 10~80 (mL/g), and the more preferred ratio is 30~50 (mL/g). Furthermore, in order to destroy the reductant so as to terminate step (3), glacial acetic acid is preferably added to terminate said step.

5. Step (4) and Step (7) of the Present Invention

Step (4) and step (7) of the present invention relate to the formation of soluble Rosuvastatin salt (for instance, Rosuvastatin sodium) via alkaline hydrolysis of Rosuvastatin ester. Wherein, reactions of step (4) and step (7) proceed in the presence of solvent, and said solvent can be selected from THF, alcohol or acetonitrile, and the preferred solvent is acetonitrile; the reaction temperature of said step (4) and step (7) is −10~80° C., and the preferred temperature is 20~40° C.; the molar ratio between NaOH and Rosuvastatin ester of said step (4) and step (7) is 1.05~2.0:1, and the preferred ratio is 1.1:1. Furthermore, after the completion of the reaction of step (7), in order to remove impurities, the product obtained from step (7) is extracted with water-immiscible solvent, and the preferred water-immiscible solvent is ethyl acetate or ethyl ether.

6. Step (5) of the Present Invention

Rosuvastatin acid is syrupy, and it is relatively unstable as well as is easy to convert to Rosuvastatin lactone. Therefore, as for conversion of Rosuvastatin acid from Rosuvastatin sodium, the preferred conditions are as follows: water insoluble solvent is added to aqueous solution of Rosuvastatin sodium, subsequently, inorganic acid or organic acid is added to said mixture, in this way, Rosuvastatin acid is dissociated and dissolves in said water-immiscible solvent. Wherein, the preferred solvent is selected from ester, ether, or halohydrocarbon, and the most preferred solvent is ethyl ether. Furthermore, the added inorganic acid or organic acid is selected from hydrochloric acid, sulfuric acid, formic acid or glacial acetic acid, and the preferred acid is hydrochloric acid. After the addition of inorganic acid or organic acid, the pH value of said reaction system is controlled to be at 1~6, and the preferred pH value is 3~5. The acidification temperature is normally below 40° C., and it is preferred that the reaction mixture is continuously mixed so that the dissociated Rosuvastatin acid could dissolve in water insoluble solvent. Subsequently, the obtained is allowed to stand for layering, the water phase is extracted with water insoluble solvent and then combined and dried. It is preferred that a certain amount of alkali (for instance, $Na_2CO_3$, $K_2CO_3$ or other weak bases) is added during the condensation of acid so as to reduce the reaction rate of lactonization as side reaction.

7. Step (6) of the Present Invention

Esterification of Rosuvastatin acid should be carried out in the absence of acid. As under acidic condition, especially when the strong acid is present and the reaction temperature is relatively high, Rosuvastatin acid is very easy to convert to Rosuvastatin lactone, and allylic (5-hydroxyl) racemization is easy to take place. Preparation of Rosuvastatin ester from Rosuvastatin acid is preferred to be performed under alkaline or neutral conditions, however, under said conditions, lactonization could not be prevented, and the formed ester could still convert to lactone at relatively high reaction temperature in the presence of alkali if the reaction time is relatively long. To solve these problems, especially to ensure a relatively high yield during the multi-step reaction of present invention, it is shown in present invention that the effective utilization rate of Rosuvastatin is not significantly influenced by hydrolysis-esterification of the present invention, the utilization rate of Rosuvastatin during formation of Rosuvastatin sodium via hydrolysis reaches 97~99%, and the overall yield of said two steps is above 94%. Wherein, the esterification of Rosuvastatin acid and alkylation reagent takes place under the alkaline condition, and the preferred alkylation reagent is halohydrocarbon, wherein the preferred halogen atom is selected from Cl, Br, or I, the more preferred halogen is Br or I, and the most preferred halohydrocarbon $R^3X$ is 1-bromo-3-methylbutane. Other practicable alkylation reagents could be alkyl tosylate, alkyl trifluoromethanesulfonate ester and the like. The preferred alkali is selected from carbonate, bisulfate, biphosphate, dihydric phosphate, and the preferred alkali is $K_2CO_3$; said alkali could also be organic base, for example organic amine, such as triethylamine. The preferred ratio is 1.0 eq~5.0 eq for halohydrocarbon, and the more preferred ratio is 1.1 eq~3.0 eq; 1.0 eq~3.0 eq for alkali, and the more preferred ratio is 1.0 eq~1.5 eq.

The reaction of said step (6) can be preformed in the presence of solvent, wherein said solvent is selected from ketone, DMF, DMSO, or HMPA, and the preferred solvent is DMF or acetone. Wherein the reaction temperature range is between −40° C. and 80° C., the preferred temperature range is between 0° C. and 60° C., the more preferred temperature range is between 10° C. and 50° C., and the most preferred temperature range is between 20° C. and 40° C. If the solubility of solid alkali in the solvent is relatively low, phase transfer catalyst could be added to facilitate the reaction, and said phase transfer catalyst can be selected from quaternary ammonium salt, crown ether or polyethylene glycol. The preferred amount of phase transfer catalyst ranges from 0.2 eq to 1.5 eq. When methyl iodide is used in the preparation of Rosuvastatin methyl ester in said step (6), the preferred conditions are as follows: 3.0 eq methyl iodide, 1.2 eq $K_2CO_3$, the reaction temperature is 20° C., and 1.0 eq phase transfer catalyst tetrabutyl ammonium bromide. When 1-bromo-3-methylbutane is used in the preparation of Rosuvastatin isopentyl ester, the preferred conditions are as follows: 2.5 eq 1-bromo-3-methylbutane, 1.1 eq $K_2CO_3$, and the reaction temperature is 40° C.

After the reaction of step (6) is finished, the resultant of reaction needs to be purified. The product obtained from said step (6) is preferred to be purified via recrystallization, and the solvent of said recrystallization is selected from ester, ether, alcohol or aqueous solutions thereof, and the preferred solvent is ethyl ether or isopropyl ether.

8. Step (8) of the Present Invention

The preferred molar ratio between calcium acetate (or $CaCl_2$) and compound as shown in Formula 7 is 1.0~1.2:2, and the more preferred ratio is 1.05~1.1:2. Wherein, it is more preferred that compound as shown in Formula 7 converts to calcium acetate of compound as shown in Formula 1 in the presence of calcium acetate, and the most preferred molar ratio between calcium acetate and compound as shown in Formula 7 is 1.05:2 or 1.1:2.

In order to further recover compound as shown in Formula 1 in the mother liquid, the step involving further recovery of compound as shown in Formula 1 of the mother liquid is preferred. This means that after the reaction of step (8) is finished, compound as shown in Formula 1 is separated, subsequently, the remaining aqueous solution is acidified and extracted with ethyl ether, and NaOH is added to dissolve said extractant, and then $CaCO_3$ is added, as a result, compound as shown in Formula 1 is formed. The quality of the product recovered from water phase is similar to that of the directly synthesized product. The obtained highly purified Rosuvastatin ester could almost be fully used.

9. Application of Steps of the Present Invention

Modifications based on the present invention can also be applied to the preparation of other Rosuvastatin derivatives (for example, Rosuvastatin ester) and reprocessing of unqualified Rosuvastatin calcium. For example, when the purity of Rosuvastatin ester prepared via other synthetic route is relatively low, when the purity of Rosuvastatin lactone is lower, or when the quality of prepared Rosuvastatin salt does not meet the standard, said Rosuvastatin products could convert to Rosuvastatin acid via hydrolysis, subsequently, the obtained is treated according to step (6) or step (6) to step (7) of the present invention and other treatment steps can follow if necessary, in this way, more qualified product is obtained. The above applications of said step of the present invention also fall in the scope of the present invention. Therefore, the present invention also relates to the application of step (6) or step (6) to step (7) in the purification of Rosuvastatin ester, Rosuvastatin lactone or Rosuvastatin salt, wherein it comprises the conversion of Rosuvastatin acid from Rosuvastatin ester, Rosuvastatin lactone or Rosuvastatin salt, and then step (6) or step (6) to step (7) of the present invention is carried out.

10. Crystalline Rosuvastatin Intermediate and its Application

Rosuvastatin ester intermediate is obtained according to the method of the present invention. Since the preparation method of the present invention is used, the purity of said intermediate is high and the amount of impurities that might influence crystallization is lowered, and the recrystallization with regular solvent known to the skilled in the art could be applied to obtain Rosuvastatin ester crystal. For example, the prepared (3R,5S,6E)-7-[4-(4-fluorophenyl)-6-(1-methyl ethyl)-2-[methyl(methylsulfonyl)amino]-5-pyrimidyl]-3,5-dihydroxyl-6-methyl heptenoate could be recrystallized in the presence of ethyl ether, thus crystalline product is obtained, and the product has a spectrum of powder XRD showing peak values at 2θ=8.7, 9.3, 9.6, 17.4, 18.0, 19.5, 21.7, 24.4, 24.7 and 26.3. The prepared (3R,5S,6E)-7-[4-(4-fluorophenyl)-6-(1-methyl ethyl)-2-[methyl(methyl sulfonyl)amino]-5-pyrimidyl]-3,5-dihydroxyl-6-heptenoic-3-methyl butyrate could be refined via a number of ways, in this way, several crystalline products are obtained. For instance, a mixed solvent containing ethyl ether and acetonitrile could be used for the recrystallization, and the obtained crystalline product (crystal form I) has a spectrum of powder XRD showing peak values at 2θ=9.5, 16.3, 19.3, 20.7 and 20.9; optionally, if methanol is used for the recrystallization, the obtained crystalline product (crystal form II) shall have a spectrum of powder XRD showing peak values at 2θ=9.6, 11.9, 16.6, 18.5, 19.2, 19.7 and 20.8.

Furthermore, said intermediate can be used as raw material in the preparation or purification of Rosuvastatin salt, especially it can be used in the preparation or purification of Rosuvastatin calcium. Due to the fact that the purity of these crystallized intermediates is high, the purification cost can be reduced.

The advantages of said steps of the present invention are illustrated to those skilled in the art through the above descriptions. The requirements on the purity of intermediate of the present invention are considerably lowered. The intermediates (3R,6E)-3-[[(1,1-dimethyl ethyl)dimethyl silyl]-oxo]-7-[4-(4-fluorophenyl)-6-(1-methyl ethyl)-2-[methyl (methyl sulfonyl)amino]-5-pyrimidyl]-5-oxo-6-methyl heptenoate and (3R,6E)-7-[4-(4-fluorophenyl)-6-(1-methyl ethyl)-2-[methyl(methyl sulfonyl)amino]-5-pyrimidyl]-3-hydroxy-5-oxo-6-heptenoate can also be purified without column chromatography and recrystallization, and a relatively low purity does not influence the preparation of Rosuvastatin final product, therefore, the process is relatively easy to be controlled, the product quality is reliable, the production cost is relatively low and large scale production could be realized. Highly purified Rosuvastatin calcium of the present invention normally has the purity of above 99.5%, and the purity of said Rosuvastatin calcium could be improved to 99.9% via optimization.

The present invention is further illustrated with the following examples and drawings. It should be noted that the examples and drawings are only used for illustration, and the present invention is not limited to said examples and drawings. Modifications and variants of the present invention made by those skilled in the art should be considered to fall in the scope of the present invention. Furthermore, the references of the present invention (including patent references and non-patent references) are also used for further illustration of present invention, and the full content of said references are incorporated in present invention as described in the specification of present invention.

FIG. 1 shows the test results of (3R,6E)-7-[4-(4-fluorophenyl)-6-(1-methyl ethyl)-2-[methyl(methylsulfonyl)amino]-5-pyrimidyl]-3-hydroxyl-5-oxo-6-methyl heptenoate prepared according to the example of the present invention by HPLC, and the peak parameters are summarized in Table 1:

TABLE 1

| Peak | Retention time | Area | Area % | Resolution | Theoretic plate number |
|---|---|---|---|---|---|
| 1 | 7.608 | 17664 | 0.054 | 0.000 | 90.357 |
| 2 | 8.192 | 17881 | 0.055 | 0.098 | 14.014 |
| 3 | 10.446 | 83605 | 0.256 | 0.472 | 2730.895 |
| 4 | 11.947 | 2148 | 0.007 | 1.967 | 4330.685 |
| 5 | 15.658 | 32474640 | 99.504 | 3.935 | 2913.500 |
| 6 | 19.046 | 17562 | 0.054 | 2.853 | 3931.378 |
| 7 | 21.398 | 16142 | 0.049 | 1.756 | 3418.690 |
| 8 | 23.370 | 6803 | 0.021 | 1.280 | 3344.354 |
| Total | | 32636447 | 100.000 | | |

Figure 2:
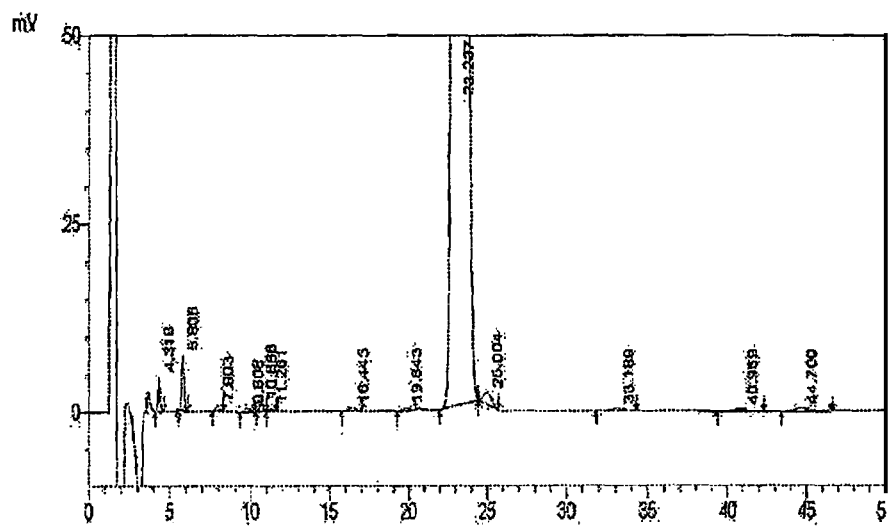
FIG. 2 shows the test results of (3R,5S,6E)-7-[4-(4-fluorophenyl)-6-(1-methyl ethyl)-2-[methyl(methyl sulfonyl)amino]-5-pyrimidyl]-3,5-dihydroxyl-6-heptenoic-3-methyl butyrate prepared according to an embodiment of the present invention by HPLC.

FIG. 2 shows the test results of (3R,5S,6E)-7-[4-(4-fluorophenyl)-6-(1-methyl ethyl)-2-[methyl(methyl sulfonyl) amino]-5-pyrimidyl]-3,5-dihydroxyl-6-heptenoic-3-methyl butyrate prepared according to the example of the present invention by HPLC, wherein the peak parameters are summarized in Table 2:

TABLE 2

| Peak | Retention time | Area | Area % | Resolution | Theoretical plate number |
|---|---|---|---|---|---|
| 1 | 4.318 | 44796 | 0.093 | 0.000 | 4321.851 |
| 2 | 5.806 | 85446 | 0.177 | 5.131 | 5358.102 |

TABLE 2-continued

| Peak | Retention time | Area | Area % | Resolution | Theoretical plate number |
|---|---|---|---|---|---|
| 3 | 7.903 | 10152 | 0.021 | 5.922 | 6531.229 |
| 4 | 9.808 | 7042 | 0.015 | 4.430 | 7004.106 |
| 5 | 10.666 | 16712 | 0.035 | 1.831 | 8276.467 |
| 6 | 11.261 | 4648 | 0.010 | 1.294 | 10030.797 |
| 7 | 16.445 | 11415 | 0.024 | 8.962 | 8651.683 |
| 8 | 19.843 | 9301 | 0.019 | 4.652 | 11095.459 |
| 9 | 23.237 | 48028824 | 99.369 | 3.907 | 8921.603 |
| 10 | 25.004 | 57365 | 0.119 | 1.751 | 9353.314 |
| 11 | 33.189 | 11643 | 0.024 | 6.596 | 8407.785 |
| 12 | 40.969 | 20952 | 0.043 | 4.864 | 8756.737 |
| 13 | 44.700 | 25384 | 0.053 | 2.085 | 9579.857 |
| Total | | 48333680 | 100.000 | | |

Figure 3:
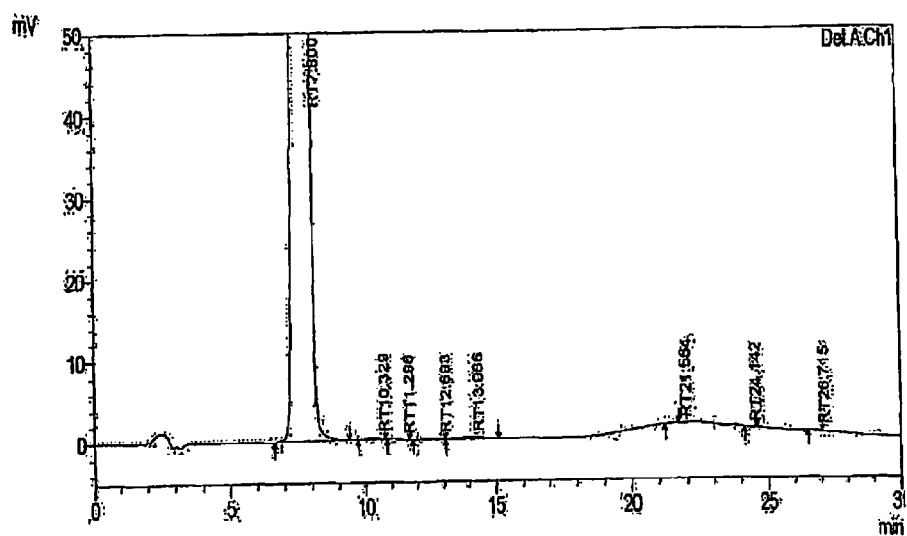
FIG. 3 shows the test result of Rosuvastatin calcium prepared according to an embodiment of the present invention by HPLC.

FIG. 3 shows the test result of Rosuvastatin calcium prepared according to the example of the present invention by HPLC, wherein the peak parameters are summarized in Table 3:

TABLE 3

| Peak | Retention time | Area | Area % | Resolution | Theoretical plate number |
|---|---|---|---|---|---|
| 1 | 7.800 | 20834061 | 99.848 | 0.000 | 2375.082 |
| 2 | 10.329 | 8252 | 0.040 | 3.466 | 2541.630 |
| 3 | 11.296 | 2826 | 0.014 | 1.177 | 3014.550 |
| 4 | 12.693 | 2040 | 0.010 | 1.545 | 2653.774 |
| 5 | 13.966 | 15040 | 0.072 | 0.966 | 1147.680 |
| 6 | 21.564 | 1264 | 0.006 | 7.032 | 28380.267 |
| 7 | 24.142 | 784 | 0.004 | 5.498 | 51465.381 |
| 8 | 26.715 | 1483 | 0.007 | 5.442 | 42227.859 |
| Total | | 20865748 | 100.000 | | |

Figure 4:
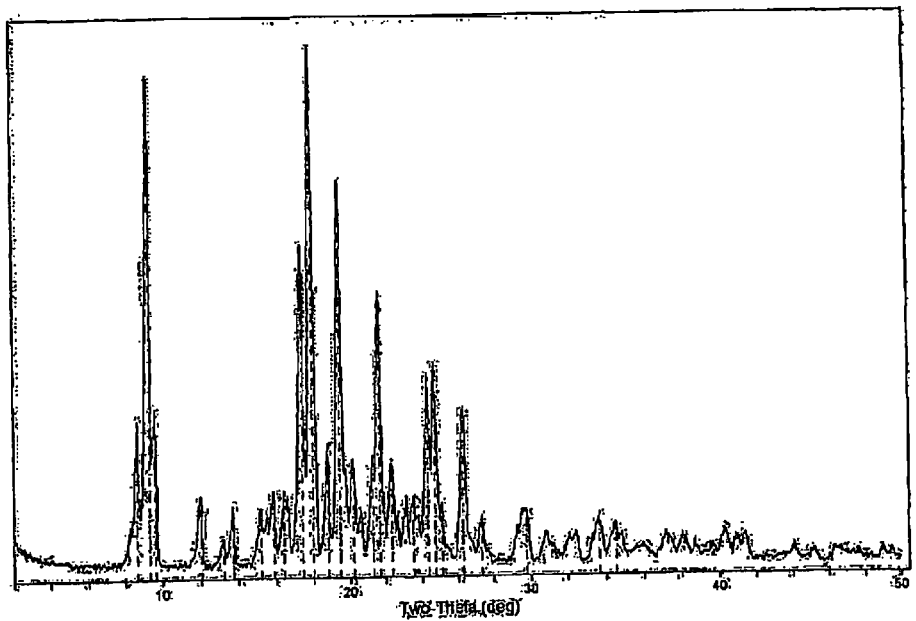
FIG. 4 shows the results of powder XRD of (3R,5S,6E)-7-[4-(4-fluorophenyl)-6-(1-methyl ethyl)-2-[methyl(methyl sulfonyl)amino]-5-pyrimidyl]-3,5-dihydroxyl-6-methyl heptenoate prepared according to an embodiment of the present invention.

FIG. 4 shows the results of powder XRD of (3R,5S,6E)-7-[4-(4-fluorophenyl)-6-(1-methyl ethyl)-2-[methyl(methyl sulfonyl)amino]-5-pyrimidyl]-3,5-dihydroxyl-6-methyl heptenoate prepared according to the example of the present invention, wherein the peak parameters are summarized in Table 4:

TABLE 4

| 2θ | d- (Å) | Relative intensity (%) |
|---|---|---|
| 8.7 | 10.2 | 27 |
| 9.3 | 9.5 | 96 |
| 9.6 | 9.2 | 30 |
| 17.4 | 5.1 | 59 |
| 18.0 | 4.9 | 100 |
| 19.5 | 4.5 | 71 |
| 21.7 | 4.1 | 47 |
| 24.4 | 3.7 | 31 |
| 24.7 | 3.6 | 38 |
| 26.3 | 3.4 | 29 |

Figure 5:
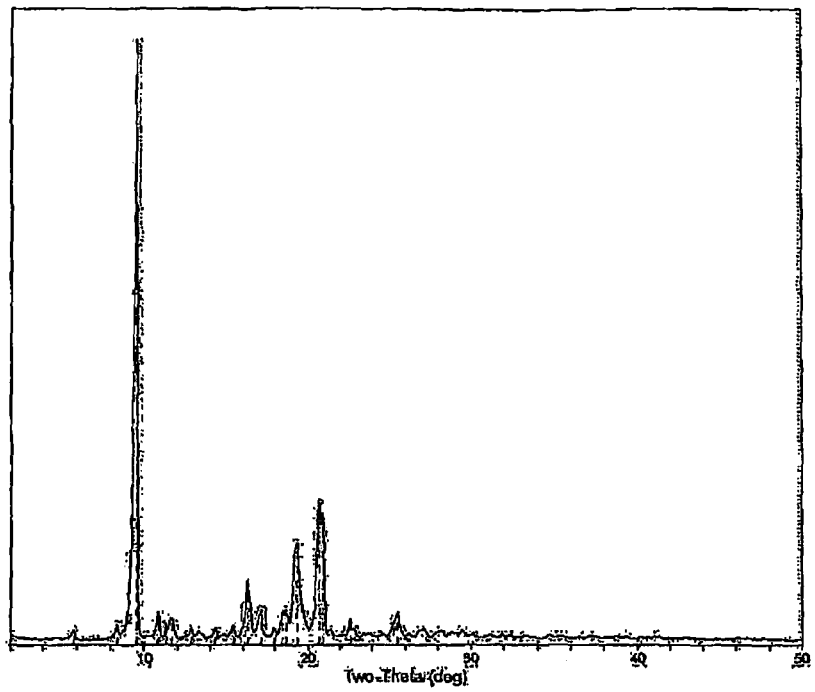
FIG. 5 shows the results of powder XRD of crystal form I of (3R,5S,6E)-7-[4-(4-fluorophenyl)-6-(1-methylethyl)-2-[methyl(methylsulfonyl)amino]-5-pyrimidyl]-3,5-dihydroxyl-6-heptenoic-3-methyl butyrate prepared according to an embodiment of the present invention.

FIG. 5 shows the results of powder XRD of crystal form I of (3R,5S,6E)-7-[4-(4-fluorophenyl)-6-(1-methylethyl)-2-[methyl(methylsulfonyl)amino]-5-pyrimidyl]-3,5-dihydroxyl-6-heptenoic-3-methyl butyrate prepared according to the example of the present invention, wherein the peak parameters are summarized in Table 5:

TABLE 5

| 2θ | d-(Å) | Relative intensity (%) |
|---|---|---|
| 9.5 | 9.3 | 100 |
| 16.3 | 5.4 | 9.8 |

TABLE 5-continued

| 2θ | d-(Å) | Relative intensity (%) |
|---|---|---|
| 19.3 | 4.6 | 16 |
| 20.7 | 4.3 | 24 |
| 20.9 | 4.2 | 22 |

Figure 6:
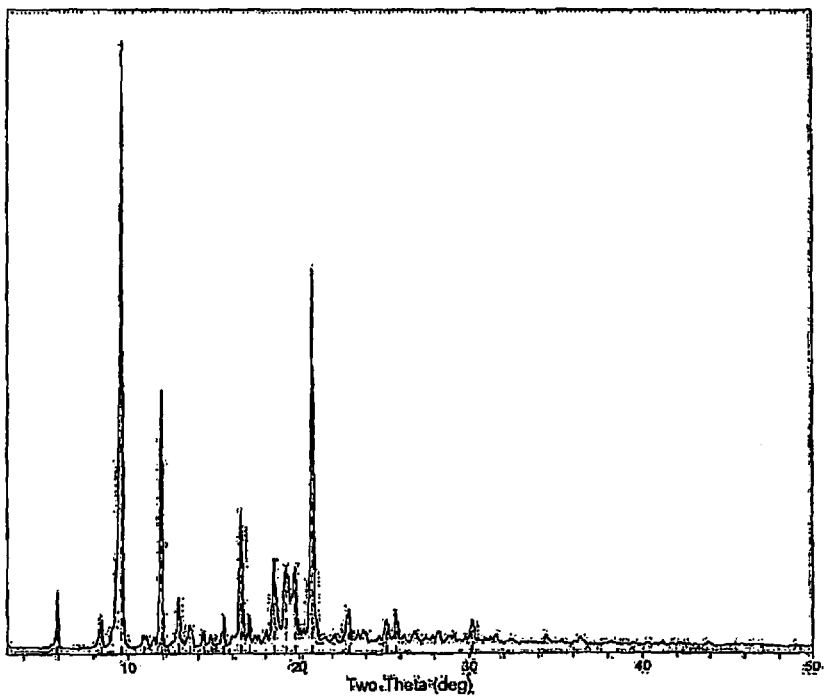
FIG. 6 shows the results of powder XRD of crystal form II of (3R,5S,6E)-7-[4-(4-fluorophenyl)-6-(1-methyl ethyl)-2-[methyl(methyl sulfonyl)amino]-5-pyrimidyl]-3,5-dihydroxyl-6-heptenoic-3-methyl butyrate prepared according to an embodiment of the present invention.

FIG. 6 shows the results of powder XRD of crystal form II of (3R,5S,6E)-7-[4-(4-fluorophenyl)-6-(1-methyl etheyl)-2-[methyl(methyl sulfonyl)amino]-5-pyrimidyl]-3,5-dihydroxyl-6-heptenoic-3-methyl butyrate prepared according to the example of the present invention, wherein the peak parameters are summarized in Table 6:

TABLE 6

| 2θ | d- (Å) | Relative intensity (%) |
|---|---|---|
| 9.6 | 9.2 | 100 |
| 11.9 | 7.4 | 42 |
| 16.6 | 5.3 | 23 |
| 18.5 | 4.8 | 14 |
| 19.2 | 4.6 | 12 |
| 19.7 | 4.5 | 11 |
| 20.8 | 4.3 | 62 |

EXAMPLES

The present invention is further illustrated via the following examples. Except specified indication, methods listed in handbook of chemical synthesis, chemical standard and references cited by the present invention could be applied to carry out the examples.

Example 1

Preparation of (3R,6E)-3-[[(1,1-dimethylethyl)dimethyl silyl]-oxo]-7-[4-(4-fluorophenyl)-6-(1-methylethyl)-2-[methyl(methylsulfonyl)amino]-5-pyrimidyl]-5-oxo-6-methyl heptenoate The synthetic route is shown in flow diagram 1:

Flow diagram 1

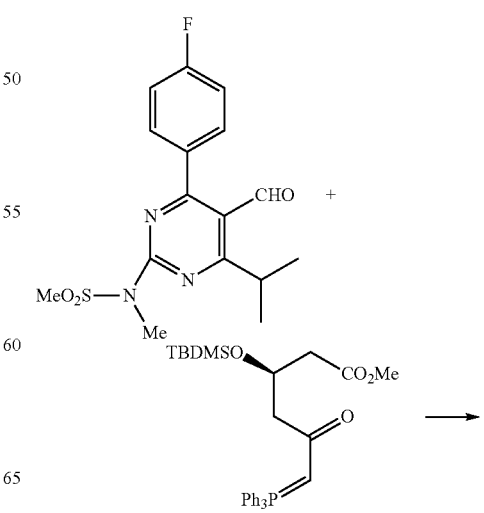

-continued

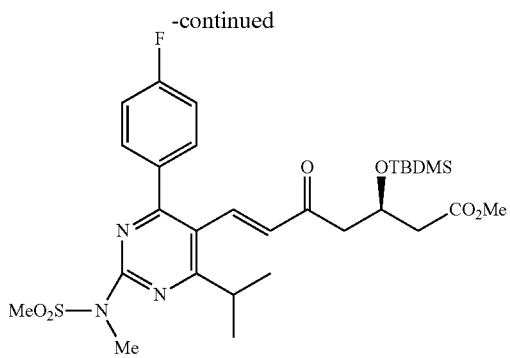

-continued

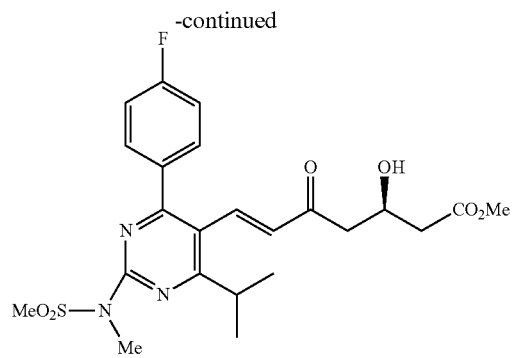

The detailed preparation process is as follows: 16 mL acetonitrile, 30.7 g (R)-3-[[(1,1-dimethyl ethyl)dimethyl silyl]oxo]-5-oxo-6-(triphenyl phosphoranylidene)-methyl hexanoate and 20.2 g N-[4-(4-fluorophenyl)-5-formyl-6-(1-methylethyl)-2-pyrimidyl]-N-methyl-methanesulfonamide were added to a 200 mL reaction flask, subsequently, the mixture was heated to 84° C. and refluxed until TLC indicated that the content of N-[4-(4-fluorophenyl)-5-formyl-6-(1-methylethyl)-2-pyrimidyl]-N-methyl-methanesulfonamide in the reaction solution did not change any more, this reaction took around 12 hours, then the reaction mixture was cooled and vacuum distilled at 50° C. to remove acetonitrile, in this way, oily product was obtained. The oily product was immediately transferred to a 500 mL reaction flask, subsequently, 345 mL cyclohexane was added, the mixture was heated and refluxed for 20 minutes, and then the reaction mixture was cooled to 5° C. and stirred for 5 hours until solid precipitated, the obtained was filtered to remove the solid, the filter cake was washed twice with cyclohexane (40 mL each time), and then the washing solution was combined with filtrate. The obtained filtrate was vacuum distilled to remove organic solvent cyclohexane at 45° C., as a result, 46 g oily (3R,6E)-3-[[(1,1-dimethyl ethyl)dimethyl silyl]-oxo]-7-[4-(4-fluorophenyl)-6-(1-methyl ethyl)-2-[methyl(methyl sulfonyl) amino]-5-pyrimidyl]-5-oxo-6-methyl heptenoate was obtained.

Example 2

Preparation of (3R,6E)-7-[4-(4-fluorophenyl)-6-(1-methylethyl)-2-[methyl(methyl sulfonyl)amino]-5-pyrimidyl]-3-hydroxy-5-oxo-6-methyl heptenoate The synthetic route is as shown in flow diagram 2:

Flow diagram 2

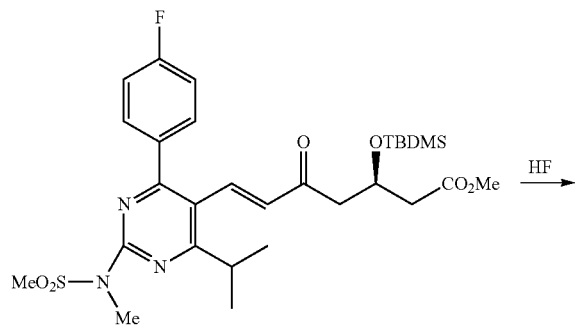

HF →

The detailed preparation process is as follows: 290 mL acetonitrile and 46 g (3R,6E)-3-[[(1,1-dimethyl ethyl)dimethyl silyl]-oxo]-7-[4-(4-fluorophenyl)-6-(1-methyl ethyl)-2-[methyl(methyl sulfonyl)amino]-5-pyrimidyl]-5-oxo-6-methyl heptenoate of Example 1 were added to a 2000 mL reaction flask, and the mixture was cooled to 0° C., and then acetonitrile solution containing HF (70 mL 40% HF+1090 mL acetonitrile) was added at constant speed at 5° C., this addition process took 2.5 hours. Subsequently, the mixture was heated to 28° C. and mixed until TLC showed that the content of raw material in the reaction solution was less than 1%, the mixing took around 4 hours, and then the reaction finishes. 300 mL saturated sodium bicarbonate solution was added to the reaction solution, subsequently, solid sodium bicarbonate was added to adjust the pH value until it reached 8, the mixture was stirred for 20 minutes, and then it was allowed to stand for layering, wherein the water phase was collected, the organic phase was washed twice with saturated sodium chloride solution (250 mL each time), the solution was stirred for 15 minutes during each washing, the obtained was allowed to stand for layering, and the saturated sodium chloride solution phase was collected. 15 g anhydrous sodium sulfate was added to the organic phase and stirred for 35 minutes, the organic phase was filtered to remove anhydrous sodium sulfate, and the obtained filtrate was vacuum distilled to remove the organic solvent at 50° C., as a result, crude product A was obtained.

Furthermore, all the collected water phase was combined and washed twice by ethyl acetate (450 mL each time), the water phase was stirred for 15 minutes during each washing, subsequently, the obtained was allowed to stand for layering, the collected organic phase was combined and washed twice with saturated sodium chloride solution (500 mL each time), the organic phase was stirred for 15 minutes during each washing, subsequently, the obtained was allowed to stand for layering, then the water phase was removed, 5 g anhydrous sodium sulfate was added and stirred for 35 minutes, and the obtained was filtered to remove anhydrous sodium sulfate. The filtrate was vacuum distilled to remove organic solvent at 50° C., as a result, crude product B was obtained.

The obtained crude product A and crude product B were combined and added to a 200 mL reaction flask, and 80 mL ethanol was added, subsequently, the mixture was heated in a water bath and refluxed, then the temperature of the mixture was cooled to −15° C. within 120 minutes, the mixture was stirred for 12 hours until solid precipitated, and the obtained was filtered, the filter cake was washed with 20 mL ethyl ether, and then was dried at 45° C. for 6 hours under vacuum, as a result, 24.5 g yellow solid was obtained.

The yellow solid, 25 mL acetone and 125 mL isopropyl ether were added to a 200 mL reaction flask, heated and mixed (the temperature was controlled at 70° C. so that the yellow solid can be dissolved), subsequently, the mixture was cooled to 23° C. The temperature was cooled to −15° C. within 3 hours later, and the obtained was allowed to stand for 24 hours until solid precipitated, then the obtained was filtered, the filter cake was washed with 10 mL isopropyl ether at 0° C., as a result, yellow solid was obtained. The yellow solid was placed in a vacuum drier and dried at 45° C. for 6 hours, in this way, 22.5 g (3R,6E)-7-[4-(4-fluorophenyl)-6-(1-methyl ethyl)-2-[methyl(methylsulfonyl)amino]-5-pyrimidyl]-3-hydroxy-5-oxo-6-methyl heptenoate was obtained.

Example 3

Preparation of (3R,5S,6E)-7-[4-(4-fluorophenyl)-6-(1-methyl ethyl)-2-[methyl(methyl sulfonyl)amino]-5-pyrimidyl]-3,5-dihydroxy-6-methyl heptenoate The synthetic route is shown in flow diagram 3:

Flow diagram 3

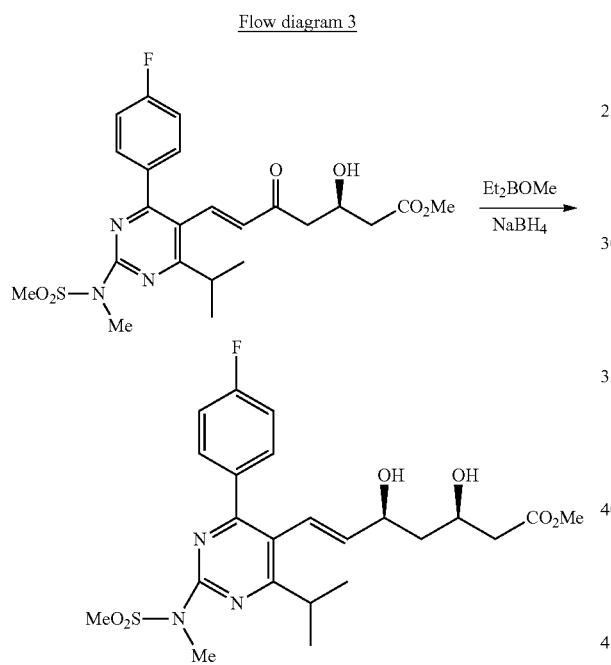

The detailed preparing process is as follows: 300 mL anhydrous THF, 85 mL anhydrous methanol and 6.3 g (3R,6E)-7-[4-(4-fluorophenyl)-6-(1-methylethyl)-2-[methyl(methyl sulfonyl) amino]-5-pyrimidyl]-3-hydroxy-5-oxo-6-methyl heptenoate were added to a 500 mL reaction flask, subsequently, the reaction system was substituted with $N_2$, and the mixture was stirred until the solid was dissolved. The reaction mixture was cooled to −85° C. by using liquid nitrogen, and 12.8 mL THF solution containing 1M diethyl methoxyl borane was added at constant speed at −85° C. within 30 minutes. The mixture was stirred for 60 minutes at −85° C., subsequently, 0.7 g sodium borohydride was uniformly added in several portions, the addition process took about 90 minutes, and then the mixture was allowed to stand at −85° C. for 6 hours. The temperature of the mixture was increased to 30° C. within 2 hour and the reaction lasts for 3 hours at 30° C., subsequently, 1.2 g glacial acetic acid was added, the obtained was vacuum distilled to remove mixed solvent containing methanol-THF at 50° C., as a result, oily product was obtained. 50 mL methanol was added to dissolve the oily product. The obtained was vacuum distilled to remove methanol at 50° C. And then 50 mL methanol was added to dissolve the oily product, the obtained was vacuum distilled to remove methanol at 50° C., and the obtained oily product remained in the reaction flask.

Afterwards, 50 mL ethyl acetate and 50 mL water were added to the reaction flask and stirred for 15 minutes, subsequently, the mixture was allowed to stand for layering. The obtained water phase was extracted twice with ethyl acetate (30 mL each time), wherein the water phase was stirred for 15 minutes during each extraction, and the obtained was allowed to stand for layering, then the organic phase was combined and washed with saturated sodium bicarbonate solution (40 mL). Subsequently, the obtained was washed twice with saturated sodium chloride solution (40 mL each time), wherein the solution was stirred for 15 minutes during each washing, it was then allowed to stand for layering. The water phase was removed, while 2 g anhydrous sodium sulfate was added to the organic phase and stirred for 30 minutes, and then anhydrous sodium sulfate was removed via pumping filtration. The filtrate was vacuum distilled to remove ethyl acetate at 50° C., as a result, 6.0 g oily (3R,5S,6E)-7-[4-(4-fluorophenyl)-6-(1-methyl ethyl)-2-[methyl(methyl sulfonyl)amino]-5-pyrimidyl]-3,5-dihydroxy-6-methyl heptenoate was obtained, and it could directly be used in next step.

Example 4

Preparation of (3R,5S,6E)-7-[4-(4-fluorophenyl)-6-(1-methyl ethyl)-2-[methyl(methyl sulfonyl)amino]-5-pyrimidyl]-3,5-dihydroxy-6-heptonic acid The synthetic route is shown in flow diagram 4:

Flow diagram 4

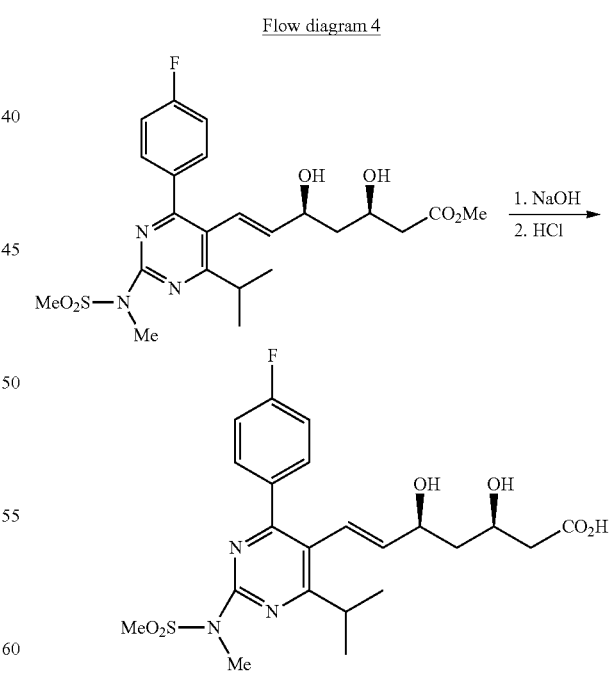

The detailed preparing process is as follows: 150 mL acetonitrile and 18 g (3R,5S,6E)-7-[4-(4-fluorophenyl)-6-(1-methyl ethyl)-2-[methyl(methyl sulfonyl)amino]-5-pyrimidyl]-3,5-dihydroxy-6-methyl heptenoate were added to a 500 mL reaction flask, once the product was fully dissolved, 40 mL purified water was added and the mixture was heated to 40° C., subsequently, 42 mL 1N sodium hydroxide solution was added at constant speed, wherein the addition process took around 15 minutes, and then the mixture was reacted at 40° C. for 2.5 hours, the obtained was vacuum distilled to remove acetonitrile at 45° C., 30 mL water was then added, the mixture was cooled to 30° C. with ice water, the mixture was washed three times with ethyl ether (50 mL each time), wherein it was stirring for 15 minutes during each washing, the obtained was allowed to stand for layering, and the water phase was collected, then 3 g activated carbon was added, the mixture was heated to 40° C. and stirred for 60 minutes, the obtained was filtered, the filter cake was washed with 10 mL purified water, the filtrate and washing solution were combined and cooled to 20° C., and then 90 mL ethyl ether was added, the pH value was adjusted to 5 with 0.5N hydrochloric acid, the mixture was stirred for 15 minutes and allowed to stand for layering for 15 minutes, the water phase was extracted twice with ethyl ether (60 mL each time), wherein it was stirring for 15 minutes during each extraction, and then was allowed to stand for layering, the organic phase was combined and washed twice with saturated sodium chloride solution (60 mL each time), it was then allowed to stand for layering, the water phase was removed, while 6 g anhydrous sodium sulfate was added to the organic phase and stirred for 35 minutes, the obtained was filtered to remove anhydrous sodium sulfate, the filtrate was vacuum distilled to remove ethyl ether at 30° C., then 50 g DMF and 2.5 g $K_2CO_3$ were added, the mixture was vacuum distilled for 1.5 hours at 30° C. to remove ethyl ether, as a result, 69.6 g DMF solution containing (3R,5S,6E)-7-[4-(4-fluorophenyl)-6-(1-methyl ethyl)-2-[methyl(methyl sulfonyl)amino]-5-pyrimidyl]-3,5-dihydroxy-6-heptonic acid was obtained.

Example 5

Preparation of (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate The synthetic route is shown in flow diagram 5:

Flow diagram 5

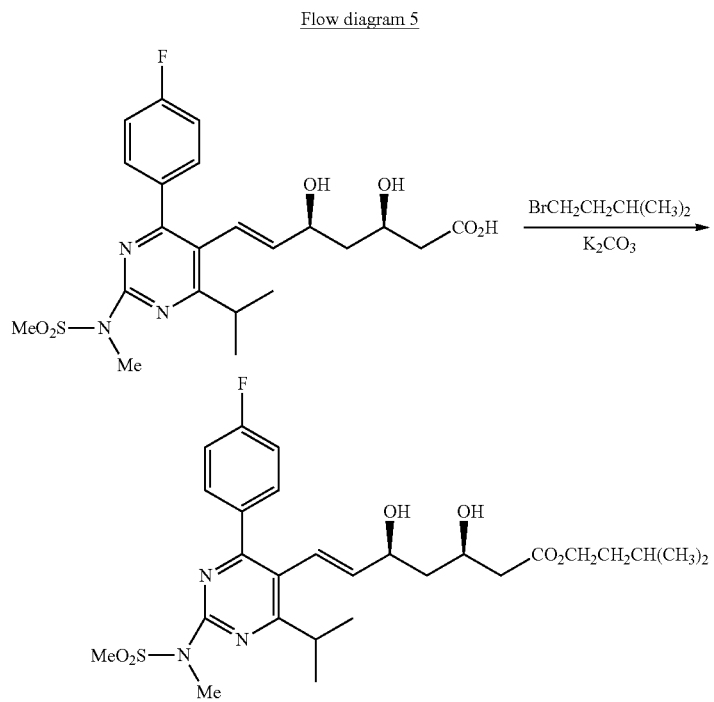

The detailed preparation process is as follows: 200 mL DMF, 69.6 g DMF solution containing (3R,5S,6E)-7-[4-(4-fluorophenyl)-6-(1-methyl ethyl)-2-[methyl(methyl sulfonyl)amino]-5-pyrimidyl]-3,5-dihydroxy-6-heptonic acid (including about 2.5 g $K_2CO_3$) prepared by the Example 4, 26.8 g 1-bromo-3-methylbutane, 13.2 g tetrabutylammonium bromide and 17.3 g potassium iodide were added to a 500 mL reaction flask and then heated to 40° C., the mixture was reacted until TLC indicated that the content of raw materials in the reaction solution was less than 1%, the reaction took around 2.5 h; subsequently, 660 mL water and 340 mL ethyl acetate were added in sequence, the mixture was stirred for 15 minutes and allowed to stand for layering, the water phase was extracted twice with ethyl acetate (100 mL each time), the ethyl acetate phase was combined and washed three times with saturated sodium chloride solution (180 mL each time), wherein the ethyl acetate phase was stirred for 15 minutes during each washing, and then was allowed to stand for layering, 9 g anhydrous sodium sulfate was added to the organic phase, the obtained was stirred for 35 minutes, and then it was filtered to remove anhydrous sodium sulfate; then, the filtrate was transferred to a 500 mL condensation flask, the mixture was heated to 45° C. and vacuum distilled to remove ethyl acetate; the remaining was transferred to a 100 mL flask, and 80 mL isopropyl ether was added, then the mixture was stirred to be dissolved, the temperature of the mixture was increased to 75° C. and then decreased to 0° C. within 3 hours, and the stirring was stopped, the obtained was allowed to stand for devitrification for 12 hours, and then stirred for 60 minutes, the obtained was filtered and vacuum dried, as a result, 15.2 g crude product of (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate was obtained.

130 mL ethyl ether, 1.6 mL acetonitrile and the above dried crude product of (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate were added to a 100 mL reaction flask, then the mixture was heated to 40° C. and stirred for 35 minutes, at the same time, 29 mL mixed solvent containing ethyl ether and acetonitrile was distilled, the stirring was stopped, the obtained was cooled to 0° C. within 3 hours and then allowed to stand for devitrification for 12 hours. The obtained was filtered, the filter cake was washed twice with 5 mL ethyl ether, as a result, wet product of (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate was obtained. The obtained wet product was then vacuum dried at 35° C. for 5 hours, in this way, 12.5 g (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate crystal was obtained.

Example 6

Preparation of Rosuvastatin Calcium

The synthetic route is shown in flow diagram 6:

The detailed preparation process is as follows: 80 mL acetonitrile was added to a 200 mL reaction flask and stirred, subsequently, 12.5 g (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate was added to the flask and heated to 35° C., and then 25 mL purified water was added, 25 mL 1N sodium hydroxide solution was slowly added at constant speed at 40° C., wherein, the addition took 15 minutes, the mixture was kept at 40° C. and reacted for 2.5 hours, the obtained was vacuum distilled at 40° C. to remove acetonitrile, 25 mL purified water was added to the residue, the pH value was adjusted to 9 with 3 g 0.5N glacial acetic acid solution, the mixture was then cooled to 0° C. in an ice-salt bath, the water phase was washed for three times with ethyl ether (30 mL each time), the water phase was stirred for 15 minutes during each washing and then it was allowed to stand for layering, then the temperature was increased to 40° C., vacuum distillation was carried out to remove remaining ethyl ether, the water phase was filtered to a salt reaction flask and washed with 20 mL purified water, the washing solution and filtrate were combined and cooled to 20° C., then 13.5 mL 1N filtered calcium acetate was slowly added at constant speed, the addition process took about 30 minutes, and the mixture was stirred for 2 hours at 20° C., it was then filtered, the obtained solid was beat was 40 mL 20° C. purified water, it was then vacuum dried, as a result, 7.3 g Rosuvastatin calcium was obtained.

Furthermore, after the of Rosuvastatin calcium was removal by precipitation, a certain amount of Rosuvastatin calcium syill remained in the mother liquid. Therefore the present invention also preferably provides a method for the recovery of Rosuvastatin calcium in the mother liquid. The mother liquid was transferred to a 1000 mL reaction flask, Flow diagram 6

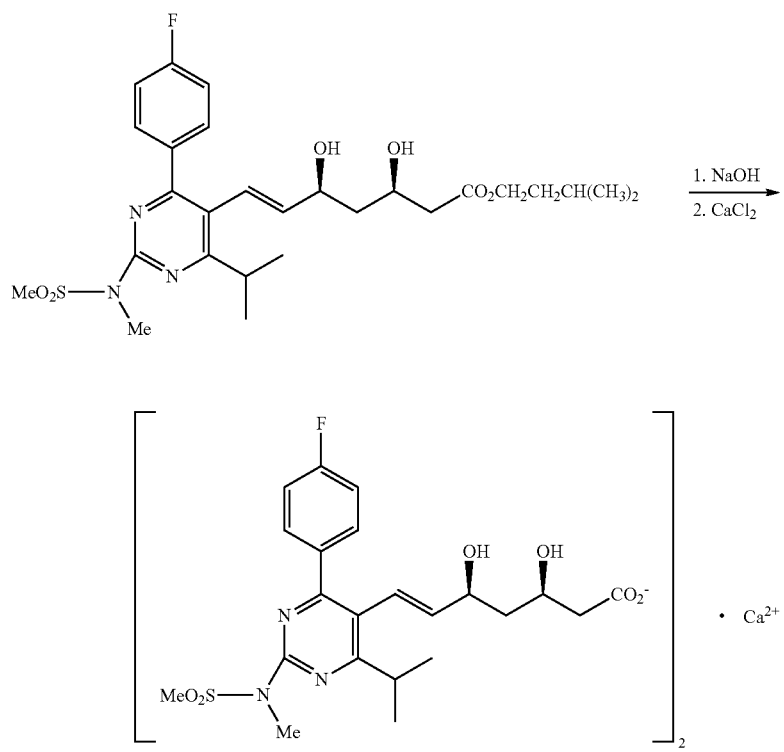

200 mL ethyl ether was added, at the same time the pH value was adjusted with 0.5N hydrochloric acid until it reached 3, then the mixture was stirred for 15 minutes and allowed to stand for layering. The water phase was washed twice with ethyl ether (100 mL each time), during each washing the water phase was stirred for 15 minutes, and then it was allowed to stand for layering, the organic phase was combined and washed twice with purified water (150 mL×2), during each washing the organic phase was stirred for 15 minutes, it was then allowed to stand for lyering, the water phase was removed, while 4 g anhydrous sodium sulfate was added to the organic phase and stirred for 30 minutes, the obtained was filtered to remove anhydrous sodium sulfate, the filtrate was then condensed. The obtained was vacuum distilled to remove ethyl ether until 300 mL ethyl ether was distilled at 40° C., subsequently, 40 mL purified water was added to the remaining, the obtained was cooled to 30° C. with icy water, 8.4 mL 1N NaOH solution was added slowly at 40° C. until the pH reached 11, the mixture was then stirred for 60 minutes, the pH value was adjusted to 9 with 2 g 0.5N glacial acetic acid, the obtained was allowed to stand for layering. The water phase was washed twice with ethyl ether (10 mL each time), during each washing the water phase was stirred for 15 minutes, then it was allowed to stand for layering, the water phase was vacuum distilled at 40° C. to remove remaining ethyl ether, then the temperature was decreased to 20° C., 5 mL 1N filtered calcium acetate was slowly added at constant speed at 20° C., the addition process took around 30 minutes, and the temperature was kept at 20° C., the mixture was stirred for 2 hours, then it was filtered, and the obtained solid was beat with 10 mL of 20° C. purified water, filtered and vacuum dried in sequence, as a result, 2.5 g Rosuvastatin calcium was obtained.

Example 7

Preparation of crystalline (3R,5S,6E)-7-[4-(4-fluorophenyl)-6-(1-methyl ethyl)-2-[methyl(methyl sulfonyl)amino]-5-pyrimidyl]-3,5-dihydroxy-6-methyl heptenoate After 30 mL ethyl ether was added to 10 g intermediate (3R,5S,6E)-7-[4-(4-fluorophenyl)-6-(1-methyl ethyl)-2-[methyl(methyl sulfonyl)amino]-5-pyrimidyl]-3,5-dihydroxy-6-methyl heptenoate of the present invention, the mixture was heated until the intermediate was fully dissolved, subsequently, it was cooled to −10-20° C. and precipitated for 20-25 hours, and the obtained was filtered and washed with ethyl ether, as a result, 7.2 g crystalline solid was obtained with the yield of 72%, and its XRD spectrum is shown in FIG. 4.

Example 8

Preparation of crystalline (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate (crystal form I)

After 80 mL ethyl ether and 1.5 mL acetonitrile was added to 10 g (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate, the mixture was heated until the mixture was fully dissolved, then it was cooled to 0~5° C. and devitrified for 24 hours, as a result, 7.7 g crystalline solid was obtained with the yield of 77%, and the XRD spectrum is shown in FIG. 5.

Example 9

Preparation of crystalline (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate (crystal form II)

After 15 mL methanol was added to 10 g intermediate (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate of the present invention, the mixture was heated until it was fully dissolved, subsequently, the obtained was cooled to 0~5° C. and devitrified for 15~20 hours, as a result, 4.5 g crystalline solid was obtained with the yield of 45%, and the XRD spectrum is shown in FIG. 6.

The invention claimed is:

1. A preparation method of a crystalline intermediate of a rosuvastatin compound of Formula I,

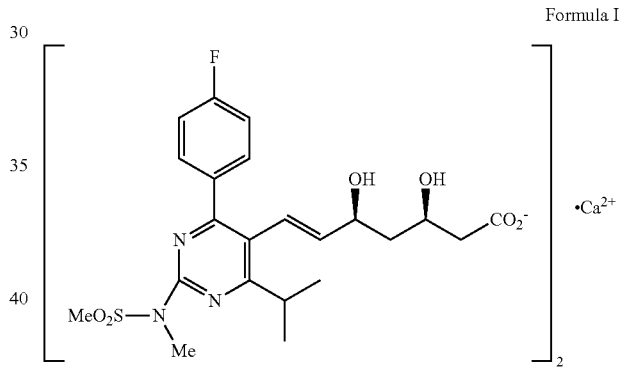

Formula I

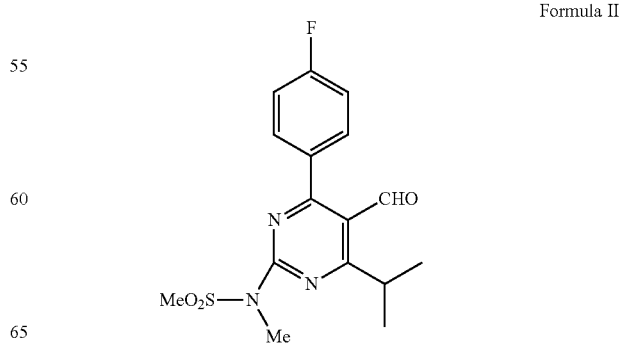

Formula II the crystalline intermediate obtained during the method comprising:

(a) conducting a Witting condensation of a compound of Formula II with a compound of Formula III to form a compound of Formula IV, -continued Formula III

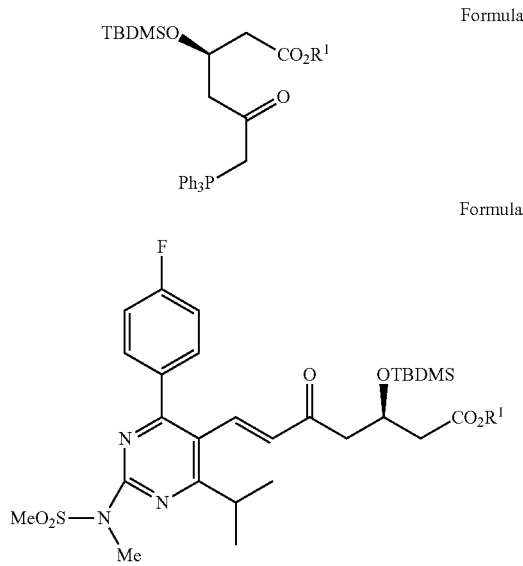

Formula IV wherein $R^1$ is a low alkyl group;

(b) deprotecting the silane group of the compound of Formula IV in the presence of hydrofluoric acid to obtain a compound of Formula V;

Formula V (c) conducting asymmetric reduction on the compound of Formula V in the presence of $R^2_2$BOMe and $NaBH_4$ to form a compound of Formula VI, Formula VI wherein $R^2$ is a $C_1$-$C_8$ linear or branched alkyl group;

(d) conducting alkaline hydration on the compound of Formula VI in the presence of sodium hydroxide to form a compound of Formula VII;

Formula VII (e) conducting acidification of the compound of Formula VII in the presence of an acid to form a compound of Formula VIII; and Formula VIII (f) conducting esterification of the compound of Formula VIII and a halohydrocarbon $R^3X$ in the presence of alkali to form a compound of Formula IX, Formula IX wherein $R^3$ is a low alkyl group or a benzyl and X is a halogen;

(g) conducting alkaline hydration on the compound of Formula IX in the presence of alkali to form the compound of Formula VII; and (h) converting the compound of Formula VII in the presence of a soluble calcium salt to the compound of Formula I,

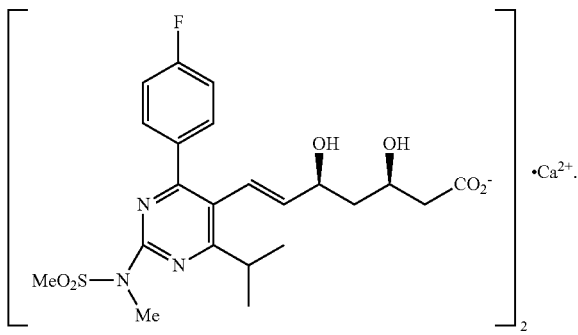

2. The method of claim 1, wherein the crystalline intermediate is chosen from (3R,5S,6E)-7-[4-(4-fluorophenyl)-6-(1-methyl ethyl)-2-[methyl(methyl sulfonyl)amino]-5-pyrimidyl]-3,5-dihydroxyl-6-methyl heptenoate, (3R,5S,6E)-7-[4-(4-fluorophenyl)-6-(1-methyl ethyl)-2-[methyl(methyl sulfonyl)amino]-5-pyrimidyl]-3,5-dihydroxyl-6-isopentyl heptenoate, and (3R,5S,6E)-7-[4-(4-fluorophenyl)-6-(1-methyl ethyl)-2-[methyl(methyl sulfonyl)amino]-5-pyrimidyl]-3,5-dihydroxyl-6-isopentyl heptenoate.

3. The method of claim 2, wherein the crystalline intermediate is (3R,5S,6E)-7-[4-(4-fluorophenyl)-6-(1-methyl ethyl)-2-[methyl(methyl sulfonyl)amino]-5-pyrimidyl]-3,5-dihydroxyl-6-methyl heptenoate, and the crystalline intermediate has a spectrum of powder XRD with peak values at 2θ=8.7, 9.3, 9.6, 17.4, 18.0, 19.5, 21.7, 24.4, 24.7 and 26.3.

4. The method of claim 3, wherein the crystalline intermediate is prepared from (3R,5S,6E)-7-[4-(4-fluorophenyl)-6-(1-methyl ethyl)-2-[methyl(methyl sulfonyl)amino]-5-pyrimidyl]-3,5-dihydroxyl-6-methyl heptenoate following step (c).

5. The method of claim 4, wherein the crystalline intermediate is prepared by recrystallizing (3R,5S,6E)-7-[4-(4-fluorophenyl)-6-(1-methyl ethyl)-2-[methyl(methyl sulfonyl)amino]-5-pyrimidyl]-3,5-dihydroxyl-6-methyl heptenoate in the presence of a solvent comprising ethyl ether.

6. The crystalline intermediate of claim 3 being used for the preparation of a Rosuvastatin salt.

7. The crystalline intermediate of claim 3 being used for the purification of a Rosuvastatin salt.

8. The method of claim 2, wherein the crystalline intermediate is (3R,5S,6E)-7-[4-(4-fluorophenyl)-6-(1-methyl etheyl)-2-[methyl(methyl sulfonyl)amino]-5-pyrimidyl]-3,5-dihydroxyl-6-isopentyl heptenoate, and the crystalline intermediate has a spectrum of powder XRD with peak values at 2θ=9.5, 16.3, 19.3, 20.7 and 20.9.

9. The method of claim 8, wherein the crystalline intermediate is prepared from (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate following step (f).

10. The method of claim 9, wherein the crystalline intermediate is prepared by recrystallizing (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate in the presence of a solvent comprising ethyl ether.

11. The method of claim 10, wherein the solvent further comprises acetonitrile.

12. The crystalline intermediate of claim 8 being used for the preparation of a Rosuvastatin salt.

13. The crystalline intermediate of claim 8 being used for the purification of a Rosuvastatin salt.

14. The method of claim 2, wherein the crystalline intermediate is (3R,5S,6E)-7-[4-(4-fluorophenyl)-6-(1-methyl ethyl)-2-[methyl(methyl sulfonyl)amino]-5-pyrimidyl]-3,5-dihydroxyl-6-isopentyl heptenoate, and the crystalline intermediate has a spectrum of powder XRD showing peak values at 2θ=9.6, 11.9, 16.6, 18.5, 19.2, 19.7 and 20.8.

15. The method of claim 14, wherein the crystalline intermediate is prepared from (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate following step (f).

16. The method of claim 15, wherein the crystalline intermediate is prepared by recrystallizing (3R,5S,6E)-7-[4-(4-fluorophenyl)-6-(1-methyl ethyl)-2-[methyl(methyl sulfonyl)amino]-5-pyrimidyl]-3,5-dihydroxy-6-heptenoic-3-methyl butyrate in the presence of a solvent comprising methanol.

17. The crystalline intermediate of claim 14 being used for the preparation of a Rosuvastatin salt.

18. The crystalline intermediate of claim 14 being used for the purification of a Rosuvastatin salt.

* * * * *